(12) United States Patent
Baltzer et al.

(10) Patent No.: US 7,759,377 B2
(45) Date of Patent: Jul. 20, 2010

(54) ACYLAMINOTHIAZOLE DERIVATIVES AND USE THEREOF AS BETA-AMYLOID INHIBITORS

(75) Inventors: Sylvie Baltzer, Strasbourg (FR); Marc Pascal, Pujaudran (FR); Viviane Van Dorsselaer, Strasbourg (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/051,924

(22) Filed: Mar. 20, 2008

(65) Prior Publication Data
US 2008/0176911 A1 Jul. 24, 2008

Related U.S. Application Data

(60) Division of application No. 11/457,490, filed on Jul. 14, 2006, now Pat. No. 7,371,770, which is a continuation of application No. PCT/FR2005/000029, filed on Jan. 7, 2005.

(30) Foreign Application Priority Data

Jan. 16, 2004 (FR) .................................. 04 00388
Jul. 22, 2004 (FR) .................................. 04 08116

(51) Int. Cl.
*A61K 31/426* (2006.01)
*C07D 277/38* (2006.01)
(52) U.S. Cl. ............... 514/371; 514/616; 514/364; 548/143; 548/195; 564/152
(58) Field of Classification Search .......... 514/364, 514/371; 548/143, 195
See application file for complete search history.

(56) References Cited

U.S. PATENT DOCUMENTS 7,371,770 B2 * 5/2008 Baltzer et al. .......... 514/371
2004/0152747 A1 8/2004 Chen et al.

FOREIGN PATENT DOCUMENTS

WO WO 03/014095 2/2003
WO WO 2004/009565 1/2004
WO WO 2004/033439 4/2004

OTHER PUBLICATIONS

Vippagunta et al., Advanced Drug Delivery Reviews, p. 1.*
Vippagunta et al., Advanced Drug Delivery Reviews, vol. 48, p. 3-26, 2001.*

* cited by examiner

*Primary Examiner*—Yong Chu
(74) *Attorney, Agent, or Firm*—Balaram Gupta

(57) ABSTRACT

Compounds of formula (I) as defined herein:

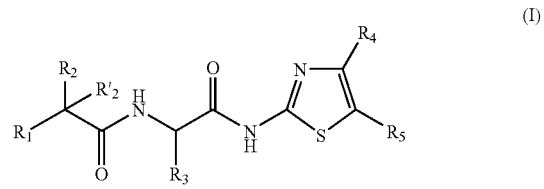

inhibit the formation of the β-amyloid peptide (β-A4) and are, therefore, useful in the treatment of pathologies in which a β-amyloid peptide (β-A4) formation inhibitor provides a therapeutic benefit. Particular such pathologies are senile dementia, Alzheimer's disease, Down's syndrome, Parkinson's disease, amyloid angiopathy, cerebrovascular disorders, frontotemporal dementias and Pick's disease, post-traumatic dementias, pathologies linked to neuroinflammatory processes, Huntington's disease and Korsakov's syndrome.

6 Claims, No Drawings

ACYLAMINOTHIAZOLE DERIVATIVES AND USE THEREOF AS BETA-AMYLOID INHIBITORS

CROSS-REFERENCE TO RELATED APPLICATIONS

This application is a division of U.S. application Ser. No. 11/457,490, filed Jul. 14, 2006, now allowed, which is a continuation of PCT/FR2005/000029, filed Jan. 7, 2005, which claims priority from French Patent Applications Nos. 0400388, filed Jan. 16, 2004, and 0408116, filed Jul. 22, 2004.

SUMMARY OF THE INVENTION

The present invention relates to acylaminothiazole derivatives, their preparation and their therapeutic use.

BACKGROUND OF THE INVENTION

Already known are acylaminothiazole derivative compounds which are described in documents WO03/014095 A and WO2004/033439 A and which inhibit the formation of the β-amyloid peptide (β-A4).

There still exists a need to find and to develop products which inhibit the formation of the β-amyloid peptide (β-A4). The compounds of the invention respond to this aim.

DETAILED DESCRIPTION OF THE INVENTION

The present invention first provides compounds conforming to the general formula (I):

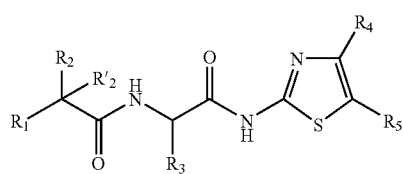

(I)

in which $R_1$ represents either a $C_{1-6}$ alkyl optionally substituted by one to three substituents selected from a halogen, a trifluoromethyl, a hydroxyl, a $C_{1-6}$ alkoxy, a $C_{1-6}$ thioalkyl, a thiophene or a phenyl; or a $C_{3-7}$ cycloalkyl, a thiophene, a benzothiophene, a pyridinyl, a furanyl or a phenyl; the said phenyl groups being optionally substituted by one to three substituents selected from a halogen atom, a $C_{1-6}$ alkyl, a $C_{1-6}$ alkoxy, a hydroxyl, a methylenedioxy, a phenoxy, a benzyloxy or a trifluoromethyl;

$R_2$ and $R'_2$ represent independently of one another a hydrogen atom, a halogen atom, a hydroxyl, a $C_{1-3}$ alkoxy, a $C_{1-3}$ alkyl, a $C_{3-7}$ cycloalkyl or an O—C(O)—$C_{1-6}$ alkyl group, or $R_2$ and $R'_2$ together form an oxo group;

$R_3$ represents either a hydrogen atom or a $C_{1-6}$ alkyl optionally substituted by a hydroxyl, a $C_{1-6}$ cycloalkyl or a $C_{1-3}$ alkoxy;

$R_4$ and $R_5$ represent independently of one another a hydrogen atom, a $C_{1-7}$ alkyl, a trifluoromethyl, a group L or a group Z;

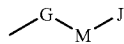

(L)

G represents a $C_{1-7}$ alkyl or a single bond;

M represents a $C_{3-7}$ cycloalkyl, a phenyl, a naphthyl or a pyridinyl, the group M being optionally substituted by one or more groups selected from a halogen atom, a hydroxyl group, a $C_{1-3}$ alkyl, a $C_{1-3}$ alkoxy, a trifluoromethyl, a trifluoromethoxy and a —O—$CHF_2$;

J represents a hydrogen atom or a group —Y—K;

Y represents a single bond, an oxygen or sulphur atom, a —$C_{1-4}$ alkylene-, —O—$C_{1-4}$ alkylene- or —$C_{1-4}$ alkylene-O— group or a group —N(W)—, the —$C_{1-4}$ alkylene-group being optionally substituted by a hydroxyl or $C_{1-3}$ alkoxy group;

W represents either a hydrogen atom, or a $C_{1-3}$ alkyl optionally substituted by a phenyl, or a phenyl;

K represents a phenyl or pyridinyl group, the group K being optionally substituted by one or more groups selected from a halogen atom, a hydroxyl group, a $C_{1-3}$ alkyl, a $C_{1-3}$ alkoxy, a trifluoromethyl, a trifluoromethoxy and an —O—$CHF_2$; with the proviso that at least one group $R_4$ or $R_5$ represents a group Z;

Z represents a CN group, a group $SO_2NR_6R_7$ or a heteroaromatic group; the said heteroaromatic group being optionally substituted by a group $R_8$; $R_8$ representing either a $C_{1-4}$ alkyl which is itself optionally substituted by a CN, a phenyl or a phenoxy; or a phenyl; the said phenyl and phenoxy groups being optionally substituted by 1 to 3 groups selected from a halogen atom, a $C_{1-3}$ alkyl, a $C_{1-3}$ alkoxy and a trifluoromethyl;

$R_6$ and $R_7$ represent, independently of one another, either a hydrogen atom, or a $C_{1-6}$ alkyl group optionally substituted by a $C_{3-7}$ cycloalkyl, a $C_{3-7}$ cycloalkenyl, $C_{1-3}$ alkoxy, a phenyl, a naphthalenyl, a morpholinyl or a pyridinyl; or a $C_{3-7}$ cycloalkyl, $C_{1-6}$ alkoxy, a phenyl or an indanyl; the said $C_{3-7}$ cycloalkyl, $C_{3-7}$ cycloalkenyl, phenyl, naphthalenyl, morpholinyl, pyridinyl and indanyl groups being optionally substituted by one or two groups selected from a $C_{1-3}$ alkyl, a hydroxyl, a $C_{1-3}$ alkoxy, a phenyl or a halogen atom; or $R_6$ and $R_7$ with the nitrogen atom which carries them form an aziridine, azetidine, pyrrolidine, piperidine, morpholine or benzopiperidine ring.

Among the compounds of general formula (I) a first subgroup of compounds is composed of the compounds for which:

$R_1$ represents a $C_{1-6}$ alkyl or a phenyl which is optionally substituted by 1 to 3 halogen atoms; and/or $R_2$ and $R'_2$ represent independently of one another a hydrogen atom or a hydroxyl; and/or $R_3$ represents a $C_{1-6}$ alkyl; and/or $R_4$ and $R_5$ represent independently of one another a hydrogen atom, a $C_{1-7}$ alkyl, a trifluoromethyl, a group L or a group Z;

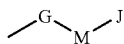 (L)

G represents a $C_{1-7}$ alkyl or a single bond; and/or

M represents a phenyl which is optionally substituted by one or more halogen atoms; and/or J represents a hydrogen atom or a group —Y—K; and/or Y represents a single bond, an oxygen atom or —O—$C_{1-4}$ alkylene-; and/or K represents a phenyl group which is optionally substituted by one or more groups selected from a halogen atom, a $C_{1-3}$ alkyl and a trifluoromethyl;

with the proviso that at least one group $R_4$ or $R_5$ represents a group Z; and/or Z represents a CN group, a group $SO_2NR_6R_7$ or a heteroaromatic group; the said heteroaromatic group being optionally substituted by a group $R_8$; $R_8$ representing either a $C_{1-4}$ alkyl which is itself optionally substituted by a phenyl; or a phenyl; and/or $R_6$ and $R_7$ represent, independently of one another, either a hydrogen atom, or a $C_{1-6}$ alkyl group optionally substituted by a phenyl or by a naphthalenyl; or a phenyl or an indanyl; the said phenyl groups being optionally substituted by one or two groups selected from a $C_{1-3}$ alkoxy, a phenyl or a halogen atom; or $R_6$ and $R_7$, with the nitrogen atom which carries them, form a benzopiperidine ring.

The compounds for which simultaneously $R_1$, $R_2$, $R'_2$, $R_3$, $R_4$, $R_5$, G, M, J, Y, K, Z, $R_6$, $R_7$ and $R_8$ are as defined in the first subgroup of compounds above form a second subgroup.

Among the compounds of general formula (I) and the subgroups above, a third subgroup of compounds is composed of the compounds for which:

$R_1$ represents a $C_{1-4}$ alkyl, preferably an isopropyl or a tert-butyl, or a phenyl substituted by two fluorine atoms; and/or $R_2$ and $R'_2$ represent independently of one another a hydrogen atom or a hydroxyl; and/or $R_3$ represents a $C_{1-4}$ alkyl, preferably a methyl, ethyl or propyl.

In the context of the present invention:

$C_{t-z}$, where t and z may take the values from 1 to 7, is understood to mean a carbon chain which can have from t to z carbon atoms, for example, $C_{1-3}$, a carbon chain which can have from 1 to 3 carbon atoms, $C_{3-6}$, a carbon chain which can have from 3 to 6 carbon atoms; and so on;

alkyl is understood to mean a linear or branched saturated aliphatic group: for example, a $C_{1-6}$ alkyl group represents a linear or branched carbon chain of from 1 to 6 carbon atoms, more particularly a methyl, ethyl, propyl, 1-methylethyl, butyl, isobutyl, sec-butyl, tert-butyl, and so on, preferably a methyl, ethyl, propyl or 1-methylethyl;

alkylene is understood to mean a linear or branched saturated divalent alkyl group: for example, a $C_{1-3}$ alkylene group represents a divalent carbon chain of from 1 to 3 carbon atoms which is linear or branched, more particularly a methylene, ethylene, isopropylene or propylene;

cycloalkyl is understood to mean a cyclic alkyl group: for example, a $C_{3-7}$ cycloalkyl group represents a cyclical carbon chain of from 3 to 7 carbon atoms, more particularly a cyclopropyl, cyclobutyl, cyclopentyl, cyclohexyl or cycloheptyl, preferably a cyclopentyl or cyclohexyl;

cycloalkenyl is understood to mean a mono- or polyunsaturated cyclic alkyl group: for example, a $C_{3-7}$ cycloalkenyl group represents a mono- or polyunsaturated cyclical carbon chain of from 3 to 7 carbon atoms, more particularly a cyclopropenyl, cyclobutenyl, cyclopentenyl, cyclohexenyl or cycloheptenyl, preferably a cyclopentenyl or cyclohexenyl;

thioalkyl is understood to mean an S-alkyl group having a linear or branched, saturated aliphatic chain;

alkoxy is understood to mean an O-alkyl group having a linear or branched, saturated aliphatic chain;

halogen atom is understood to mean a fluorine, a chlorine, a bromine or an iodine;

"$R_2$ and $R'_2$ together form an oxo group" is intended to mean the group such that:

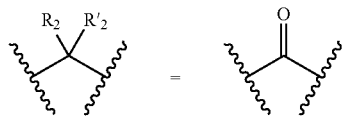

heteroaromatic group is understood to mean a cyclic aromatic group containing between 1 and 10 carbon atoms and between 1 and 4 heteroatoms, such as nitrogen, oxygen or sulphur. Examples that may be mentioned of heteroaromatic groups include oxazolyl, oxadiazolyl, tetrazolyl and benzoxazolyl groups, etc.

The compounds of general formula (I) may include one or more asymmetric carbons. They may therefore exist in the form of enantiomers or diastereoisomers. These enantiomers and diastereoisomers, and their mixtures, including the racemic mixtures, form part of the invention. When the carbon carrying $R_2$ and $R'_2$ and/or the carbon carrying $R_3$ are asymmetric, preference is given to the compounds of general formula (I) for which the carbon carrying $R_2$ and $R'_2$ is of (S) configuration and/or the carbon carrying $R_3$ is of (S) configuration.

The compounds of formula (I) may exist in the form of bases or of addition salts with acids. Such addition salts form part of the invention.

These salts are advantageously prepared with pharmaceutically acceptable acids, although the salts of other acids useful, for example, for the purification or isolation of compounds of formula (I) also form part of the invention.

The compounds of general formula (I) may occur in the form of hydrates or solvates, in other words in the form of associations or combinations with one or more molecules of water or with a solvent. Such hydrates and solvates likewise form part of the invention.

The present invention secondly provides processes for preparing the compounds of formula (I).

Thus these compounds may be prepared by processes, illustrated in the schemes below, whose operating conditions are conventional for the person skilled in the art.

A protective group is understood to mean a group which makes it possible to block the reactivity of a functional group or position in the course of a chemical reaction which might affect it, and which restores the molecule after cleavage according to methods known to the person skilled in the art. Examples of protective groups and of methods of protection and deprotection are given, inter alia, in *Protective groups in Organic Synthesis*, Greene et al., 2nd Ed. (John Wiley & Sons, Inc., New York).

The meanings of $R_1$, $R_2$, $R'_2$, $R_3$, $R_4$, $R_5$, G, M, J, Y, K, Z, $R_6$, $R_7$ and $R_8$ in the compounds of formula (II) to (XXI) below are as defined for the compounds of formula (I), unless any other definition is specified.

According to Scheme 1 below, the compound of formula (I) may be obtained by peptide coupling of the 2-aminothiazole of formula (III) with the acylamino acid of formula (II) according to conditions which are known to the person skilled in the art: for example, in the presence of benzotriazol-1-yloxytris-(pyrrolidino)phosphonium hexafluorophosphate (PyBOP) or of benzotriazol-1-yloxytris(dimethylamino)phosphonium hexafluorophosphate (BOP) and of N-1-ethylmorpholine or N-methylmorpholine in an inert solvent such as N,N-dimethylformamide, acetonitrile or dichloromethane at a temperature which may range from 0° C. to the ambient temperature.

The compound of formula (II) may be obtained by peptide coupling of the compound of formula (IV) with the protected acid of formula (V), in which Pg represents a protective group, for example a benzyl, according to methods which are known to the person skilled in the art, as described above.

The compound thus obtained is subsequently deprotected. Where the protection is a benzyl the compound is hydrogenated beforehand in the presence of palladium on carbon in absolute ethanol at atmospheric hydrogen pressure, at ambient temperature, to give the compound of formula (II).

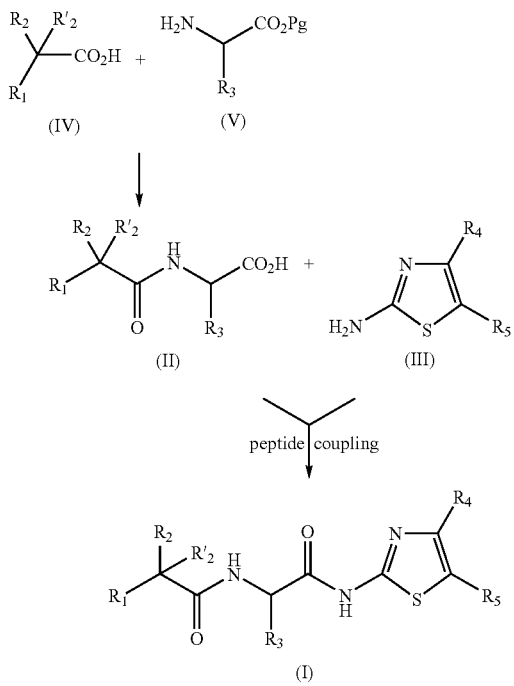

Alternatively, the compound of formula (I) may be prepared according to Scheme 2 below.

According to Scheme 2 the compound of formula (I) may be obtained by peptide coupling of the compound of formula (IV) with the amine of formula (VI), according to methods which are known to the person skilled in the art, such as, for example, in the presence of hydroxybenzotriazole hydrate (HOBt) and of 1-ethyl-3-(3-dimethylaminopropyl)carbodiimide hydrochloride (EDAC HCl).

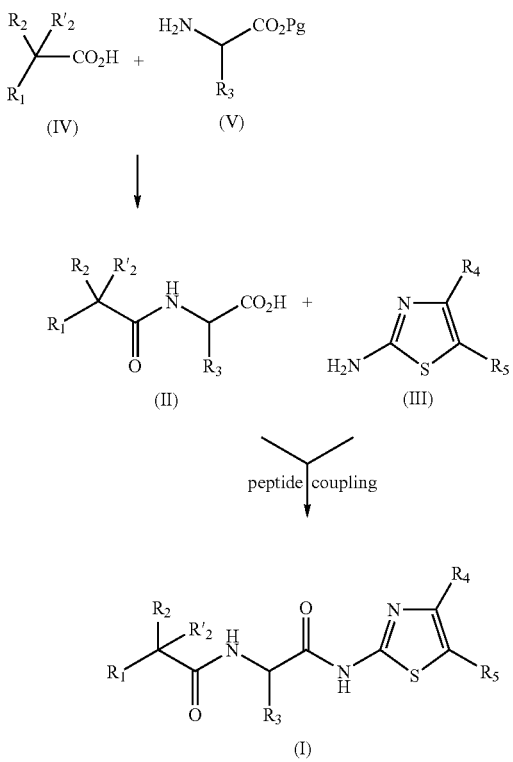

The compound of formula (VI) may be obtained by peptide coupling of the 2-aminothiazole of formula (III) with the protected amine of formula (VII), in which Pg represents a protective group, for example an N-tert-butoxycarbonyl (Boc), according to methods which are known to the person skilled in the art, as described above. The compound thus obtained is subsequently deprotected. Where the protection is a Boc the deprotection is accomplished by acidic hydrolysis in the presence of gaseous hydrochloric acid in solution in an anhydrous solvent or of trifluoroacetic acid, to give the compound of formula (VI). The compounds of formula (I) in which $R_2$ and $R'_2$ form an oxo group may be obtained by oxidizing a hydroxyl of the compound of formula (I) in which $R_2$ or $R'_2$ represents a hydroxyl group. The reaction may be carried out according to the conditions which are known to the person skilled in the art, for example with the Dess Martin reagent. These compounds may also be obtained by direct coupling of a keto acid of formula (IV), in which $R_2$ and $R'_2$ together form an oxo group, with an amine of formula (VI) according to the conditions which are known to the person skilled in the art. The methods of preparing such keto acids are known to the person skilled in the art.

The compounds of formula ($R_1$) in which $R_4$ or $R_5$=Z, where Z represents a CN group or a group of heteroaromatic type, may be prepared in accordance with Schemes 3 to 6 below.

The compounds of general formula (IIIa) and (IIIb), i.e. the compounds of general formula (III) in which $R_4$ or $R_5$ represents an oxadiazole group, may be obtained according to the methods illustrated by Schemes 3 and 4 below.

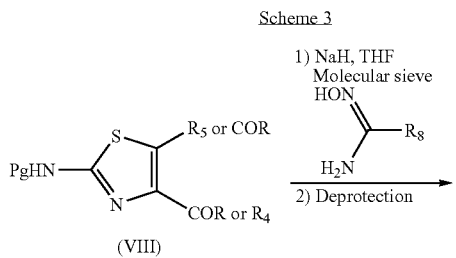

represents a protective group such as a tert-butoxycarbonyl group (Boc), with an amide oxime of formula $H_2NC(=NOH)R_8$ in anhydrous tetrahydrofuran at reflux in the presence of sodium hydride and of 4 Å molecular sieve in powder form. The compound thus obtained is subsequently deprotected according to the conditions which are known to the person skilled in the art.

According to Scheme 4 below, the compound of formula (X) is obtained by peptide coupling of the compound of formula (IX), in which Pg represents a protective group such as a Boc, with ammonia, in the presence for example of HOBt and of EDAC HCl. The compound of formula (X) may subsequently be reacted with trifluoroacetic anhydride (TFAA) in the presence of a base, for example triethylamine, to give the compound of formula (XI).

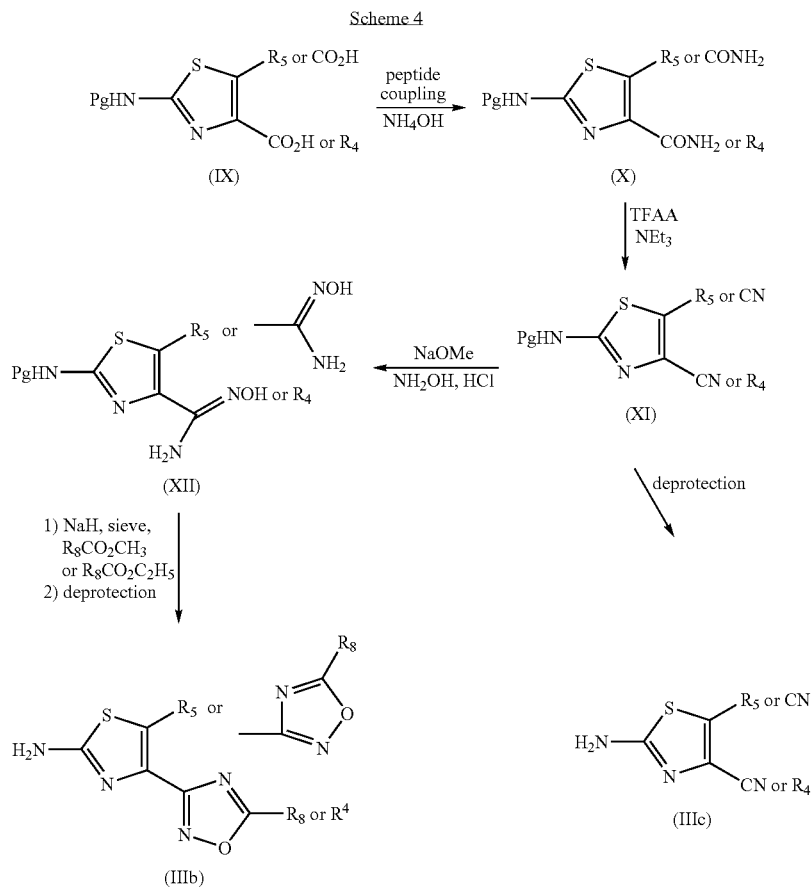

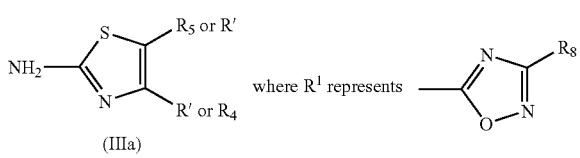

According to Scheme 3 above, the compound of formula (EIIa) may be obtained by reacting the compound of formula (VIII), in which R represents a $C_{1-6}$ alkoxy group and Pg The compound of formula (XII) may be obtained by addition of hydroxylamine HCl to the compound of formula (XI) in the presence of a base, for example sodium methoxide, according to an adaptation of the process described by Moloney et al. (J. Chem. Soc. Perkin Trans I, 1999, p. 2725). The compound of formula (XII) may subsequently be cyclized in the presence of a base such as sodium hydride and of an ester of formula $R_8CO_2CH_3$ or $R_8CO_2C_2H_5$. The compound thus obtained is deprotected according to the conditions which are known to the person skilled in the art, to give the compound of general formula (IIIb).

The method of preparation described in Scheme 4 may also make it possible to prepare the compounds of general formula (IIIc), i.e. the compounds of general formula (III) in which $R_4$ or $R_5$ represents a —CN group, by deprotecting the compounds of formula (XI) according to the conditions which are known to the person skilled in the art.

The compounds of general formula (IIId), i.e. the compounds of general formula (III) in which $R_4$ or $R_5$ represents a benzoxazole group, may be obtained according to the method illustrated by Scheme 5 below.

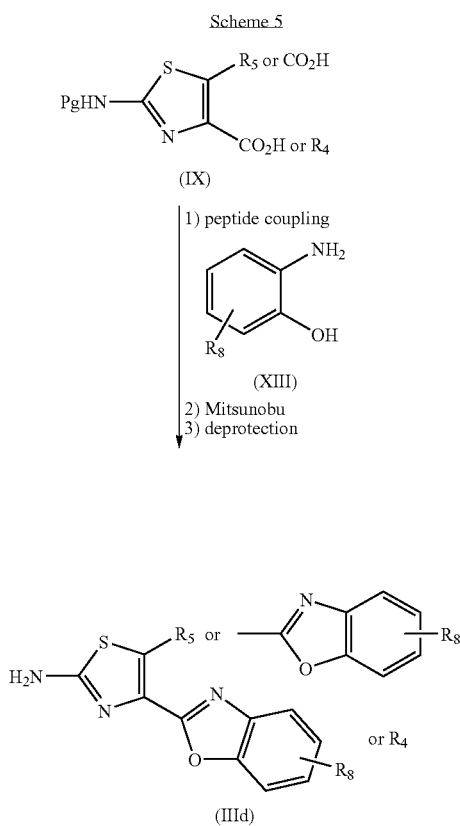

According to Scheme 5 the compound of formula (IIId) may be obtained by a peptide coupling of the compound of formula (IX) as defined above and of a compound of formula (XIII), according to the conditions which are known to the person skilled in the art, for example in the presence of benzotriazol-1-yloxytris(pyrrolidino)phosphonium hexafluorophosphate (PyBOP) or of benzotriazol-1-yloxytris(dimethylamino)phosphonium hexafluorophosphate (BOP) and of N-ethylmorpholine or N-methylmorpholine in an inert solvent such as N,N-dimethylformamide at a temperature which may range from 0° C. to the ambient temperature.

The compounds thus obtained may subsequently be cyclized by a Mitsunobu reaction according to an adaptation of the process described by Wang et al. (Tetrahedron Letters, 1997, p. 6529) and then deprotected by the methods which are known to the person skilled in the art, to give the compound of general formula (IIId).

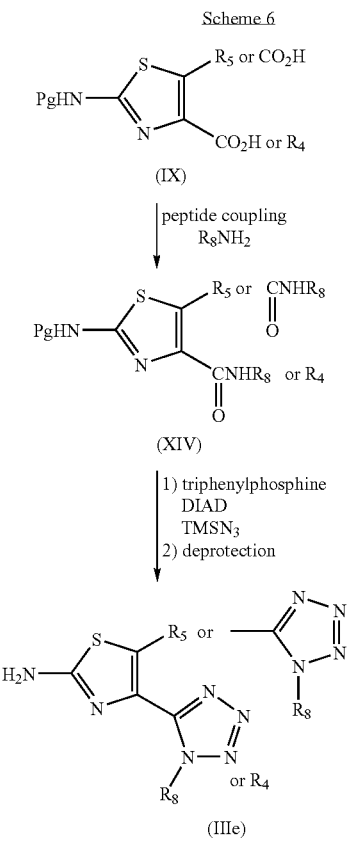

The compounds of general formula (IIIe), i.e. the compounds of general formula (III) in which $R_4$ or $R_5$ represents a tetrazole group, may be obtained according to the method illustrated by Scheme 6 above. According to Scheme 6 the compound of formula (XIV) may be obtained by peptide coupling of the compound of formula (IX) as defined above and of a primary amine of formula $R_8NH_2$ according to the conditions which are known to the person skilled in the art, for example in the presence of HOBt and EDAC HCl. The compound (XIV) thus obtained is subjected to a Mitsunobu reaction according to the conditions which are known to the person skilled in the art, for example in the presence of triphenylphosphine, diisopropyl azodicarboxylate (DIAD) and azidotrimethylsilane (TMSN$_3$), according to an adaptation of the process described by De Lombaert et al. in J. Med. Chem. 2000, p. 488. The compound obtained is subsequently deprotected by the methods which are known to the person skilled in the art, to give the compound of general formula (IIIe).

The compounds of general formula (III) in which $R_4$ or $R_5$ represents an oxazole group may be obtained starting from the corresponding aldehyde, which is itself prepared starting from the ester of formula (VIII), according to procedures which are known to the person skilled in the art, for example with p-toluenesulphonylmethyl isocyanate in the presence of a base, such as potassium carbonate or sodium methoxide, according to an adaptation of the method described by van Leusen et al. (Tetrahedron Letters, 1972, p. 2369).

The compound of formula (VIII), as defined above, may be obtained by protecting a compound of formula (IIIo),

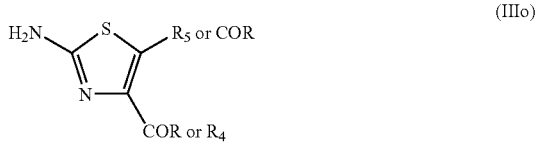

(IIIo)

for example, when Pg represents a Boc group, by the action of di-tert-butyl dicarbonate in anhydrous tetrahydrofuran in the presence of dimethylaminopyridine at ambient temperature.

The compound of formula (IX), as defined above, may be obtained by hydrolyzing the ester function of the corresponding compound of formula (VIII) according to conditions which are known to the person skilled in the art, for example with lithium hydroxide in a 7:3 (v/v) tetrahydrofuran/water mixture at a temperature of 60° C.

The compounds of formula (IIIo) may be prepared according to the methods which are illustrated by Schemes 7 and 8 below.

The compound of formula (IIIo) in which $R_4$=—C(O)R, R representing a $C_{1-6}$ alkoxy group, may be obtained according to Scheme 7 below.

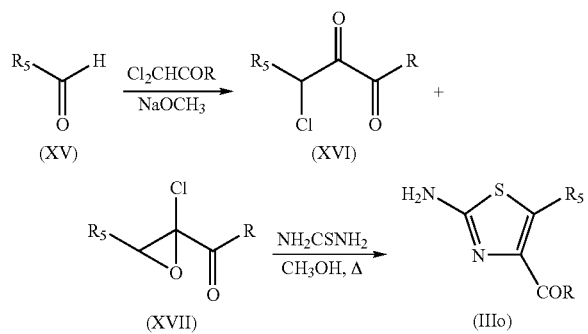

According to Scheme 7 the compound of formula (IIIo) may be obtained by reacting an aldehyde of formula (XV) with the dichloromethyl acetate of formula $Cl_2CHCOR$, in which R represents a $C_{1-6}$ alkoxy, and, for example, sodium methoxide or ethoxide at 0° C. according to an adaptation of the process described by Takeda (Bull. Chem. Soc. JP, 1970, p. 2997). The mixture of products (XVI) and (XVII) obtained is treated with thiourea in the presence for example of methanol or ethanol at reflux for 4 or 8 hours to give the compound of formula (IIIo).

The compound of formula (IIIo) in which $R_5$=—C(O)R, R representing a $C_{1-6}$ alkoxy group, may be obtained according to Scheme 8.

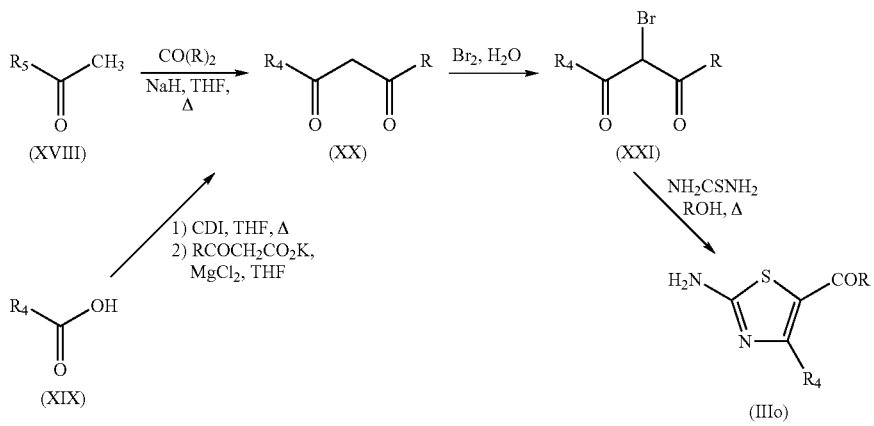

Scheme 8

According to Scheme 8 the compound of formula (IIIo) may be obtained by brominating a β-keto ester of formula (XX), in which R represents a $C_{1-6}$ alkoxy, followed by a reaction with thiourea on the compound (XXI) thus obtained, according to an adaptation of the process described by A. Barton et al. (J.C.S. Perkin I, 1982, p. 159).

The β-keto ester of formula (XX) may be obtained by reacting a ketone of formula (XVIII) with a dialkyl carbonate of formula $CO(R)_2$ in which R represents a $C_{1-6}$ alkoxy group, according to an adaptation of the process described by L. Crombie et al. (J.C.S. Perkin Trans. I, 1987, p. 323). The β-keto ester of formula (XX) may also be obtained by reacting an acid of formula (XIX), activated with carbonyldiimidazole (CDI) with a malonate of formula $RCOCH_2CO_2F$, in which R represents a $C_{1-6}$ alkoxy, according to an adaptation of the process described for example by D. W. Brooks et al. (Angew. Chem. Int. Ed., 1979, p. 72). Where $R_4$ represents a hydrogen atom the preparation of the compound of formula (XX) is accomplished according to an adaptation of the process described for example by R. Zhao et al. in Tetrahedron Letters, 2001, p. 2101.

The compounds of formula (III) in which $R_4$ or $R_5$=Z, where Z represents a group $SO_2NR_6R_7$, may be prepared starting from the corresponding sulphonyl chlorides, which are available commercially, or starting from compounds described in the literature (for example by R. P. Fatheree et al. in WO 99/26932A1, by I. T. Barnish et al. in J. Med. Chem., 1980, p. 117 and by R. Fischer et al. in WO 01/047904A1), or may be prepared by methods which are described therein or which are known to the person skilled in the art.

In Schemes 1 to 8 the starting compounds and the reagents, especially the compounds of formula (II), (IV), (V), (VII), (VIII), (IX), (XIII), (XV), (XVIII), (XIX), CO(R)$_2$, RC(O)CH$_2$CO$_2$K, Cl$_2$CHCOR, R$_8$NH$_2$, R$_8$CO$_2$CH$_3$, R$_8$CO$_2$C$_2$H$_5$ and H$_2$NC(=NOH)R$_8$, when the method of preparing them is not described, are available commercially or are described in the literature, or may be prepared by methods which are described therein or which are known to the person skilled in the art.

For example, the compounds of formula (IV) where R$_2$ or R'$_2$ represents a hydroxyl may be prepared by addition of trimethylsilyl cyanide to an aldehyde according to an adaptation of the process described by D. A. Evans et al. (J.C.S., Chem. Comm. 1973, p. 55) or by the action of sodium nitrite on an alpha-amino acid according to an adaptation of the process described by I. Shinn et al. (J. Org. Chem., 2000, p. 7667).

For example, the amide oxime of the formula H$_2$NC(=NOH)R$_9$ may be obtained according to processes which are known to the person skilled in the art, for example according to the method described by Moloney et al. in J. Chem. Soc. Perkin Trans. I, 1999, p. 2725.

When a functional group of a compound is reactive, for example when R$_1$ comprises a hydroxyl, it may necessitate prior protection before reaction. The person skilled in the art will be able readily to determine the necessity of a prior protection.

The following examples describe the preparation of certain compounds in accordance with the invention. These examples are not limitative and merely illustrate the invention.

The numbers of the compounds exemplified refer to those given in the table thereafter. The elemental microanalyses and the NMR, IR or LC-MS (liquid chromatography coupled to mass spectrometry) analyses confirm the structures of the compounds obtained.

Example 1

2-{2-(S)-[2-(S)-hydroxy(3-methyl)butyrylamino]pentanoyl}amino-5-(1-methylethyl-4-(3-phenyl-1,2,4-oxadiazol-5-yl)thiazole (compound 8)

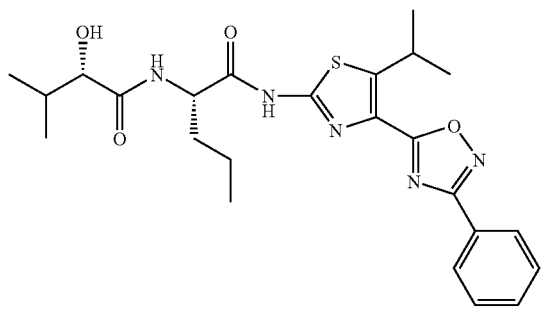

Example 1.1 methyl 2-amino-5-(1-methylethyl)thiazole-4-carboxylate

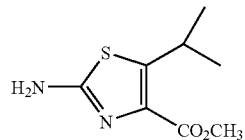

14.4 g of isobutyraldehyde in solution in 400 ml of diethyl ether are admixed at 0° C. with 24.6 g of methyl dichloroacetate and then, dropwise, with 400 ml of a solution of sodium methoxide (0.5 M) in methanol. After 1 h at 0° C. 100 ml of saturated aqueous sodium chloride solution are added and the mixture is extracted with ether. The organic phase is dried over anhydrous sodium sulphate. Solely the ether is evaporated, retaining the methanol, 8 g of thiourea are added and the mixture is heated at reflux for 6 hours. The reaction mixture is evaporated to dryness and a residue is taken up in ethyl acetate and washed with 10% aqueous ammonium hydroxide solution and then with saturated aqueous sodium chloride solution. The organic phase is dried over anhydrous sodium sulphate and then concentrated. The residue is taken up in 100 ml of ether and filtered on a frit. This gives 18.6 g of a white solid.

NMR 300 MHz (CDCl$_3$) δ ppm: 1.25 (d, 6H); 3.35 (s, 3H); 4.10 (m, 1H); 5.50 (s, 2H).

Example 1.2 methyl 2-tert-butoxycarbonylamino-5-(1-methylethyl)thiazole-4-carboxylate

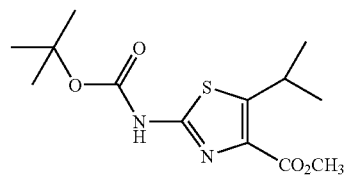

5.81 g of methyl 2-amino-5-(1-methylethyl)thiazole-4-carboxylate, obtained in step 1.1, in solution in 300 ml of tetrahydrofuran are admixed with 6.96 g of di-tert-butyl dicarbonate and 0.177 g of dimethylaminopyridine. The mixture is stirred at ambient temperature for 16 h. The reaction mixture is evaporated. The residue is taken up in ethyl acetate and washed twice with 0.5 N aqueous hydrochloric acid solution, once with water and then with saturated aqueous sodium chloride solution. The organic phase is dried over anhydrous sodium sulphate and concentrated. This gives 8.35 g of the protected aminothiazole derivative, in the form of a solid which is used as it is without purification.

LC/MS: MH$^+$=401 (M-Boc)$^+$=301.

Example 1.3

2-amino-5-(1-methylethyl)-4-(3-phenyl-1,2,4-oxa-diazol-5-yl)thiazole

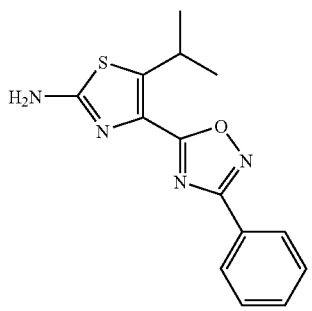

2.9 g of benzamide oxime in solution in 150 ml of tetrahydrofuran are admixed slowly at ambient temperature with 0.96 g of sodium hydride and 2 g of 4 Å molecular sieve. The mixture is heated at 60° C. for 1 h 30 min. The mixture is allowed to return to ambient temperature and then 3.6 g of methyl 2-tert-butoxy-carbonylamino-5-(1-methylethyl)thiazole-4-carboxylate, obtained in step 1.2, in 30 ml of tetrahydrofuran are added. The reaction mixture is heated at 60° C. for 12 hours. The reaction is terminated by adding water. The molecular sieve is filtered off and then the solution is concentrated. The product is taken up in ethyl acetate. Evaporation to dryness gives 3.4 g of a white solid.

3.4 g of the product obtained above in solution in 60 ml of trifluoroacetic acid are stirred at ambient temperature for 30 minutes and then evaporated. The residue is taken up in ethyl acetate and washed twice with saturated aqueous sodium carbonate solution and then with saturated aqueous sodium chloride solution. The organic phase is dried over anhydrous sodium sulphate and then evaporated, to give 1.8 g of a white solid.

NMR 300 MHz (CDCl$_3$) δ ppm: 1.38 (d, 6H); 4.21 (m, 1H); 5.23 (s, 2H); 7.50 (m, 3H); 8.20 (m, 2H).

Example 1.4

2-[2-(S)-pentanoylamino]amino-5-(1-methylethyl)-4-(3-phenyl-1,2,4-oxadiazol-5-yl)thiazole

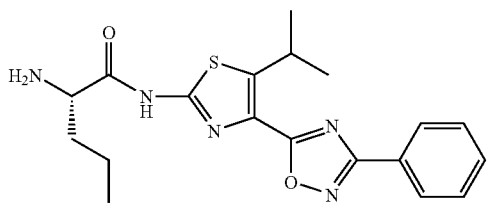

1.77 g of 2-amino-5-(1-methylethyl)-4-(3-phenyl-1,2,4-oxadizaol-5-yl)thiazole, obtained in step 1.3, in solution in 50 ml of dimethylformamide at 0° C. are admixed with 0.75 ml of N-methylmorpholine, 3.5 g of PyBOP and then 1.5 g of (S)-Bocnorvaline. The reaction mixture is allowed to return to ambient temperature and then is stirred for 16 h. Following evaporation the residue is taken up in ethyl acetate and washed twice with saturated aqueous sodium bicarbonate solution, twice with water, once with a 1H aqueous solution of potassium hydrogen sulphate and then with saturated aqueous sodium chloride solution. The organic phase is dried over anhydrous sodium sulphate and then concentrated. The residue is chromatographed on a silica gel column, eluting with a 95:5 (v/v) mixture of dichloromethane and ethyl acetate. This gives 1.4 g of a white solid.

1.4 g of the product obtained above, in solution in 60 ml of trifluoroacetic acid, are stirred at ambient temperature for 30 min and then evaporated. The residue is taken up in ethyl acetate and washed twice with saturated aqueous sodium carbonate solution and then with saturated aqueous sodium chloride solution. The organic phase is dried over anhydrous sodium sulphate and then evaporated, to give 1 g of a white solid.

NMR 300 MHz (CDCl$_3$) δ ppm: 0.98 (t, 3H); 1.45 (d, 6H); 1.62 (m, 2H); 1.92 (m, 2H); 3.64 (m, 1H); 4.25 (m, 1H); 7.50 (m, 3H); 8.20 (m, 2H).

Example 1.5

2-{2-(S)-[2-(S)-hydroxy(3-methyl)butyrylamino]pentanoyl}amino-5-(1-methylethyl-4-(3-phenyl-1,2,4-oxadiazol-5-yl)thiazole 0.2 g of 2-[2-(S)-pentanoylamino]amino-5-(1-methylethyl)-4-(3-phenyl-1,2,4-oxadiazol-5-yl)thiazole, obtained in step 1.4, in solution in 10 ml of dimethylformamide at 0° C. is admixed with 0.06 ml of N-methylmorpholine, 0.30 g of PyBOP and then 0.06 g of α-hydroxyhydrovaleric acid. The reaction mixture is allowed to return to ambient temperature and is stirred for 18 h. The reaction mixture is evaporated. The residue is taken up in ethyl acetate and washed twice with saturated aqueous sodium bicarbonate solution, twice with water, once with a 1 M aqueous solution of potassium hydrogen sulphate and then with saturated aqueous sodium chloride solution. The organic phase is dried over anhydrous sodium sulphate and then concentrated. The residue is chromatographed on a silica column, eluting with a 95:5 (v/v) dichloromethane/ethyl acetate mixture, to give 0.15 g of a white solid.

LC/MS: MH$^+$=486.

NMR: described in the table below. (compound 8)

Example 2

2-{2-(S)-[2-(S)-hydroxy(3,3-dimethyl)butyrylamino]pentanoyl}amino-5-(2-benzyloxy)phenylthiazole 4-nitrile (compound 22)

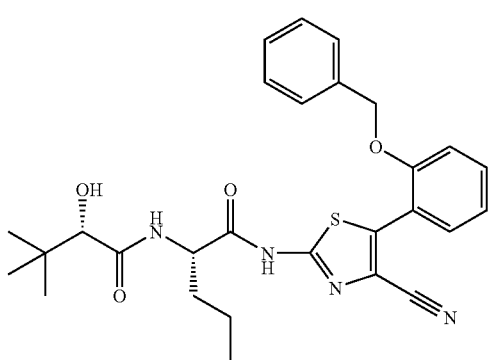

Example 2.1 methyl 2-amino-5-(2-benzyloxy)phenylthiazole 4-carboxylate

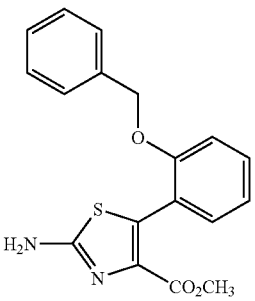

The procedure is the same as in step 1.1 of Example 1, replacing the isobutyraldehyde by 2-benzyloxybenzaldehyde (42.25 g) in solution in 400 ml of diethyl ether, to which, at 0° C., 25.7 g of methyl dichloroacetate and then, dropwise, 400 ml of a 0.5 M solution of sodium methoxide in methanol are added. After 1 h at 0° C. 100 ml of saturated aqueous sodium chloride solution are added and the mixture is extracted with ether. Treatment with thiourea (10.66 g) gives 19 g of a yellow solid.

LC/MS: $MH^+=341$.

Example 2.2 methyl 2-tert-butoxycarbonylamino-5-(2-benzyloxy) phenylthiazole-4-carboxylate

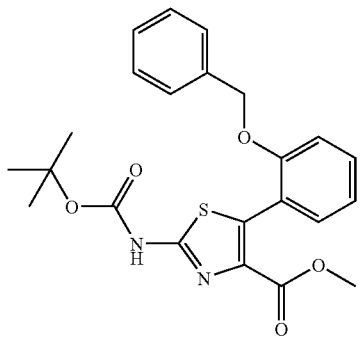

15.7 g of methyl 2-amino-5-(2-benzyloxy)phenylthiazole-4-carboxylate, obtained in step 2.1, in solution in 300 ml of tetrahydrofuran are admixed with 11.5 g of di-tert-butyl dicarbonate and 0.4 g of dimethylaminopyridine. The mixture is stirred at ambient temperature for 16 h. The reaction mixture is evaporated. The residue is taken up in ethyl acetate and washed twice with a 0.5 N aqueous hydrochloric acid solution, once with water and then with an aqueous saturated sodium chloride solution. The organic phase is dried over anhydrous sodium sulphate and concentrated. This gives 20.5 g of the protected aminothiazole derivative in the form of a solid, which is used as it is without purification.

LC/MS: $MH^+=441$ $(M-Boc)^+=341$.

Example 2.3

2-tert-butoxycarbonylamino-5-(2-benzyloxy)phenylthiazole-4-carboxylic acid

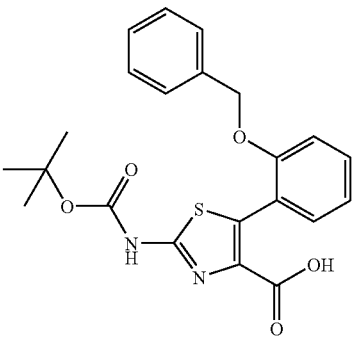

5.6 g of methyl 2-tert-butoxycarbonylamino-5-(2-benzyloxy)phenylthiazole-4-carboxylate, obtained in step 2.2, in solution in 150 ml of tetrahydrofuran are admixed at ambient temperature with a solution of 1.35 g of lithium hydroxide in 80 ml of distilled water. The reaction mixture is heated at tetrahydrofuran reflux for 16 h and then concentrated. The residue is taken up in water and washed twice with ethyl acetate. The aqueous phase is acidified with 1 N hydrochloric acid solution to a pH 4, saturated with sodium chloride and extracted twice with ethyl acetate. The organic phase is dried over anhydrous sodium sulphate and then concentrated.

LC/MS: $MH^+=427$.

Example 2.4

2-tert-butoxycarbonylamino-5-(2-benzyloxy)phenylthiazole 4-amide

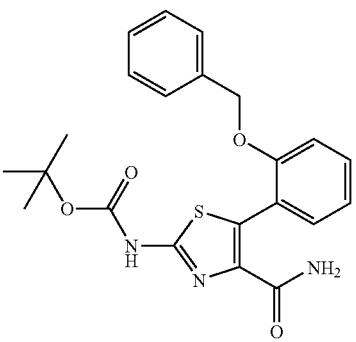

4.2 g of 2-tert-butoxycarbonylamino-5-(2-benzyloxy)phenylthiazole-4-carboxylic acid, obtained in step 2.3, in solution in 150 ml of dimethoxyethane at 0° C. are admixed with 1.3 g of N-methylmorpholine and then 1.7 g of isobutyl chloroformate and 8 ml of 25% ammonium hydroxide solution. The reaction mixture is stirred at ambient temperature for 16 h and then concentrated. The residue is taken up in ethyl acetate and washed twice with a 1 M aqueous solution of potassium hydrogen sulphate, once with water and then with saturated aqueous sodium chloride solution. The organic phase is dried over anhydrous sulphate and concentrated. The residue is chromatographed on a silica column, eluting with an 80/20 (v/v) dichloromethane/ethyl acetate mixture, to give 3.3 g of a white solid.

LC/MS: MH$^+$=426.

Example 2.5

2-tert-butoxycarbonylamino-5-(2-benzyloxy)phenylthiazole nitrile

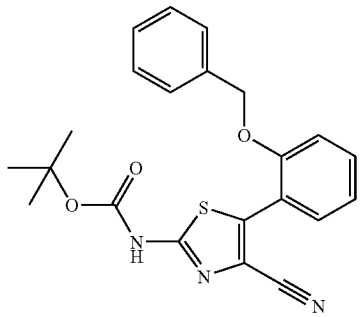

3.3 g of 2-tert-butoxycarbonylamino-5-(2-benzyloxy)phenylthiazole 4-amide, obtained in step 2.4, at 0° C. in 80 ml of dichloromethane are admixed with 2.6 ml of triethylamine and 1.7 ml of trifluoroacetic anhydride. The mixture is stirred at 0° C. for one hour and then at ambient temperature for 12 hours, and then concentrated. The residue is extracted with dichloromethane and washed twice with a 1 M aqueous solution of potassium hydrogen sulphate and then with saturated aqueous sodium chloride solution. The organic phase is dried over anhydrous sodium sulphate and then concentrated. This gives 1.1 g of a yellow solid.

LC/MS: MH$^+$=408.

NMR 300 MHz (CDCl$_3$) δ ppm: 1.55 (s, 9H); 5.22 (s, 2H); 7.00-7.80 (m, 9H).

Example 2.6

2-{2-(S)-[2-(S)-hydroxy(3,3-dimethyl)butyrylamino]pentanoyl}amino-5-(2-benzyloxy)phenylthiazole 4-nitrile The compound obtained in step 2.5 is subsequently deprotected with trifluoroacetic acid as described in step 1.3 of Example 1, then 2 successive couplings are carried out according to the processes described in steps 1.4 and 1.5 of Example 1.

This gives 0.1 g of end product.

NMR: described in the table below. (compound 22)

Example 3

2-{2-(S)-[2-(S)-hydroxy(3,3-dimethyl)butyrylamino]pentanoyl}amino-5-(2-benzyloxy)phenyl-4-(5-methyl-1,2,4-oxadiazol-3-yl)thiazole (compound 13)

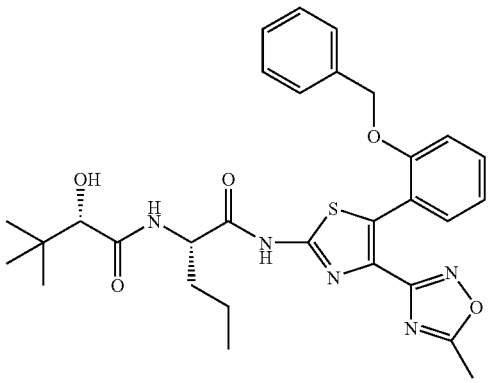

Example 3.1

2-tert-butoxycarbonylamino-5-(2-benzyloxy)phenylthiazole 4-amide oxime

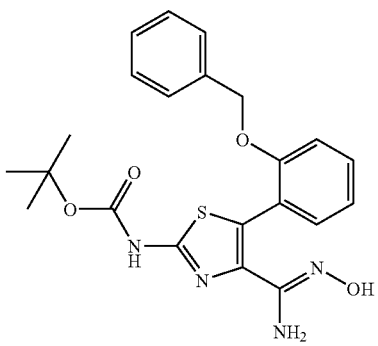

4 ml of a 0.5 M solution of sodium methoxide in methanol are admixed dropwise with 0.136 g of hydroxylamine in methanol. A white precipitate is formed and the reaction mixture is stirred at ambient temperature for one hour and then admixed with 0.8 g of the compound 2-tert-butoxycarbonylamino-5-(2-benzyloxy)phenylthiazole 4-nitrile obtained in step 2.5 of Example 2. The mixture is heated for 15 hours and then the methanol is evaporated. The residue is extracted in ethyl acetate and washed twice with saturated aqueous sodium chloride solution. The organic phase is dried over anhydrous sodium sulphate and then concentrated. This gives 0.67 g of a solid.

LC/MS: MH$^+$=441.

Example 3.2

2-tert-butoxycarbonylamino-5-(2-benzyloxy)phenyl-4-(5-methyl-1,2,4-oxadiazol-3-yl)thiazole

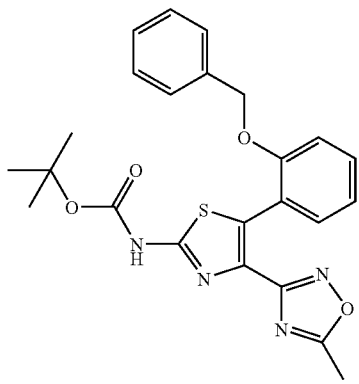

0.66 g of 2-tert-butoxycarbonylamino-5-(2-benzyloxy)phenylthiazole 4-amide oxime, obtained in step 3.1, in solution in 30 ml of tetrahydrofuran is admixed at ambient temperature slowly with 0.75 g of sodium hydride and 0.5 g of 4 Å molecular sieve. The mixture is heated at 60° C. for 1 h 30 min and then 220 µl of ethyl acetate are added and heating at 60° C. is continued for 12 h. The reaction is terminated by adding water. The molecular sieve is filtered off and the solution is concentrated. The product is taken up in ethyl acetate. Evaporation to dryness gives 0.58 g of a white solid.

NMR 300 MHz (CDCl$_3$) δ ppm: 1.53 (s, 9H); 2.48 (s, 3H); 5.04 (s, 2H); 6.90-7.42 (m, 9H); 8.00 (s, 1H).

Example 3.3

2-amino-5-(2-benzyloxy)phenyl-4-(5-methyl-1,2,4-oxadiazol-3-yl)thiazole

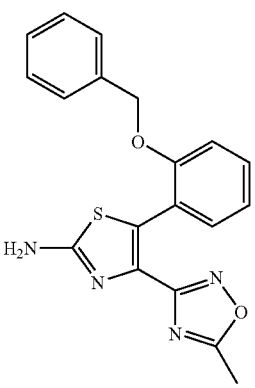

0.58 g of 2-tert-butoxycarbonylamino-5-(2-benzyloxy)phenyl-4-(5-methyl-1,2,4-oxadiazol-3-yl)thiazole, obtained in step 3.2, in solution in 30 ml of trifluoroacetic acid is stirred at ambient temperature for 30 min and then evaporated. The residue is taken up in ethyl acetate and washed twice with saturated aqueous sodium carbonate solution and then with saturated aqueous sodium chloride solution. The organic phase is dried over anhydrous sodium sulphate and then evaporated, to give 0.46 g of a white solid.

NMR 300 MHz (CDCl$_3$) δ ppm: 2.54 (s, 3H); 5.07 (s, 2H); 6.98-7.48 (m, 9H).

Example 3.4

2-{2-(S)-[2-(S)-hydroxy(3,3-dimethyl)butyrylamino]pentanoyl}amino-5-(2-benzyloxy)phenyl-4-(5-methyl-1,2,4-oxadiazol-3-yl)thiazole Two successive couplings are carried out according to the processes described in steps 1.4 and 1.5 of Example 1.

This gives 0.270 g of end product.

NMR: described in the table below. (compound 13)

LC/MS: MH$^+$=578.

Example 4

2-{2-(S)-[2-(S)-hydroxy(3,3-dimethyl)butyrylamino]pentanoyl}amino-5-(1-methylethyl)-4-(1,3-benzoxazol-2-yl)thiazole (compound 34)

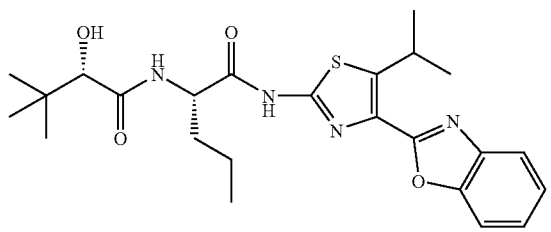

Example 4.1

2-tert-butoxycarbonylamino-5-(1-methylethyl)thiazole-4-carboxylic acid

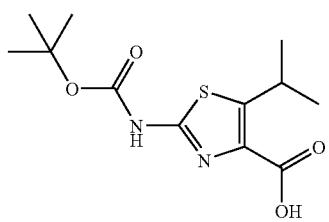

Starting from methyl 2-tert-butoxycarbonylamino-5-(1-methylethyl)thiazole-4-carboxylate, obtained in step 1.2 of Example 1, the corresponding acid (3 g) is prepared by using the process described in step 2.3 of Example 2.

LC/MS: MH$^+$=287.

NMR 300 MHz (CDCl$_3$) δ ppm: 1.20 (d, 6H); 1.50 (s, 9H); 4.40 (m, 1H).

Example 4.2

2-tert-butoxycarbonylamino-5-(1-methylethyl)thiazole 4-(2-hydroxy)phenyl carboxamide

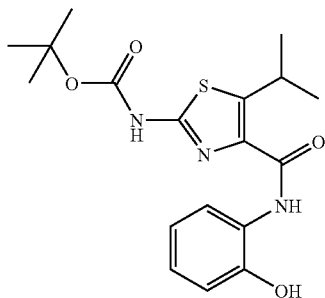

A solution of 3 g of 2-tert-butoxycarbonylamino-5-(1-methylethyl)thiazole-4-carboxylic acid, obtained in step 4.1, in 75 ml of dimethylformamide at 0° C. is admixed with 1.2 g of N-methylmorpholine, 6.11 g of PyBOP and then 1.3 g of 2-aminophenol. The reaction mixture is allowed to return to ambient temperature and is stirred for 16 h and then concentrated. The residue is taken up in ethyl acetate and washed twice with saturated aqueous sodium bicarbonate solution, twice with water, once with a 1 M aqueous solution of potassium hydrogen sulphate and then with saturated aqueous sodium chloride solution. The organic phase is dried over anhydrous sodium sulphate and then concentrated. The residue is chromatographed on a silica gel column, eluting with a mixture of petroleum ether and ethyl acetate going from 9:1 (7:3) (v/v). This gives 2.7 g of an orange-coloured powder.

LC/MS: MH$^+$=378.

NMR 300 MHz (CDCl$_3$) δ ppm: 1.35 (d, 6H); 1.36 (s, 9H); 4.33 (m, 1H); 6.80-7.20 (m, 4H); 7.78 (s, 1H); 9.30 (s, 1H); 9.52 (s, 1H).

Example 4.3

2-tert-butoxycarbonylamino-5-(1-methylethyl)-4-(1,3-benzoxazol-2-yl)thiazole

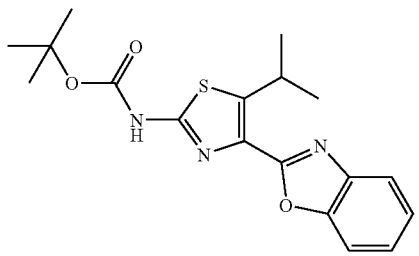

A solution of 2.72 g of 2-tert-butoxycarbonylamino-5-(1-methylethyl)thiazole 4-(2-hydroxy)phenyl carboxamide, obtained in step 4.2, in 80 ml of tetrahydrofuran at 0° C. is admixed with 2.1 g of triphenylphosphine and then, drop-wise, with 1.86 g of DIAD in 30 ml of tetrahydrofuran. The reaction mixture is slowly allowed to return to ambient temperature and is stirred for 16 h and then concentrated. The residue is chromatographed on a silica gel column, eluting with a mixture of petroleum ether and ethyl acetate going from 9:1 (7:3) (v/v). This gives 1.2 g of an orange-coloured powder.

LC/MS: MH$^+$=360.

NMR 300 MHz (CDCl$_3$) δ ppm: 1.42 (d, 6H); 1.50 (s, 9H); 4.40 (m, 1H); 7.30-7.80 (m, 4H); 8.45 (s, 1H).

Example 4.4

2-{2-(S)-[2-(S)-hydroxy(3,3-dimethyl)butyrylamino]pentanoyl}amino-5-(1-methylethyl)-4-(1,3-benzoxazol-2-yl)thiazole The 2-tert-butoxycarbonylamino-5-(1-methylethyl)-4-(1,3-benzoxazol-2-yl)thiazole obtained in step 4.3 is subsequently deprotected with trifluoroacetic acid as described in step 1.3 of Example 1, then 2 successive couplings are carried out according to the processes described in steps 1.4 and 1.5 of Example 1.

This gives 0.2 g of end product.

NMR: described in the table below. (compound 34)

LC/MS: MH$^+$=473.

Example 5

2-{2-(S)-[2-(S)-hydroxy(3,3-dimethyl)butyrylamino]pentanoyl}amino-5-(1-benzyl-1H-tetrazol-5-yl)thiazole (compound 51)

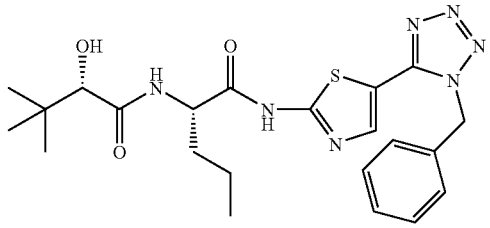

Example 5.1 methyl 2-tert-butoxycarbonylaminothiazole-5-carboxylate

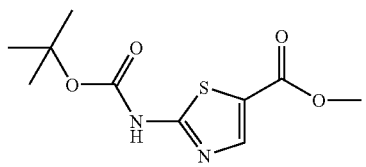

17.42 g of methyl 3-methoxyacrylate are dissolved in 200 ml of a 1/1 1,4-dioxane/water mixture and the solution is cooled to 0° C. before 29.37 g of N-bromosuccinimide are added. After 1 h at 0° C. 11.42 g of thiourea are added and then the mixture is heated at 80° C. for 2 hours. The reaction mixture is subsequently evaporated and the residue is taken up in ethyl acetate and then washed twice with 10% aqueous sodium hydroxide solution and then with saturated sodium chloride solution. The organic phase is dried over anhydrous magnesium sulphate and then concentrated.

This gives 19.17 g of a beige solid.

LC/MS: MH$^+$=159.

The amine of this intermediate is subsequently protected by a Boc group according to the process described in step 1.2 of Example 1. The mass of product obtained is 30.7 g.

LC/MS: MH$^+$=259.

NMR 300 MHz (CDCl$_3$) δ ppm: 1.50 (s, 9H); 3.80 (s, 3H); 8.06 (s, 1H).

Example 5.2

2-tert-butoxycarbonylaminothiazole 5-benzylamide

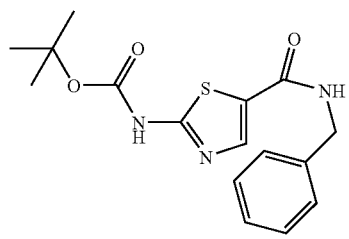

Starting from the methyl 2-tert-butoxycarbonylaminothiazole-5-carboxylate obtained in step 5.1 the corresponding acid is prepared as described in step 2.3 of Example 2. Starting from the 2-tert-butoxycarbonylaminothiazole-5-carboxylic acid thus obtained the amide (4.35 g) is prepared as described in Example 2.4.

LC/MS: MH$^+$=334.

Example 5.3

2-tert-butoxycarbonylamino-5-(1-benzyl-1H-tetrazol-5-yl)thiazole

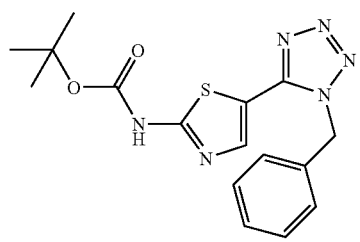

A solution of 4.35 g of the compound obtained in step 5.2 in 200 ml of tetrahydrofuran at 0° C. is admixed with 10.3 g of triphenylphosphine and then, dropwise, with 7.92 g of DIAD in 30 ml of tetrahydrofuran. After 15 minutes 4.5 g of azidotrimethylsilane, diluted in 20 ml of tetrahydrofuran, are added. The reaction mixture is allowed to return to ambient temperature and is stirred for 24 h and then concentrated. The residue is taken up in ethyl acetate and the precipitate formed is filtered off and then chromatographed on a silica gel column, eluting with a 5:5 (v/v) mixture of petroleum ether and ethyl acetate. This gives 4 g of an orange-coloured oil which is rechromatographed on a silica gel column with a mixture of dichloromethane and ethyl acetate going from 10:0 (8:2) (v/v).

LC/MS: MH$^+$=359.

NMR 300 MHz (CDCl$_3$) δ ppm: 1.50 (s, 9H); 5.92 (s, 2H); 7.18 (m, 2H); 7.37 (m, 3H); 7.98 (s, 1H); 8.86 (s, 1H).

Example 5.4

2-{2-(S)-[2-(S)-hydroxy(3,3-dimethyl)butyrylamino]pentanoyl}amino-5-(1-benzyl-1H-tetrazol-5-yl)thiazole The 2-tert-butoxycarbonylamino-5-(1-benzyl-1H-tetrazol-5-yl)-thiazole obtained in step 5.3 is subsequently deprotected with trifluoroacetic acid as described in step 1.3 of Example 1, then two successive couplings are carried out according to the processes described in steps 1.4 and 1.5 of Example 1. This gives 0.090 g of end product.

NMR: described in the table below. (compound 51)

LC/S: MH$^+$=472.6

Example 6

2-{2-(S)-[2-(3,5-difluorophenyl)acetylamino]pentanoyl}amino-4-methylthiazole 5-(N-2,3-dichlorobenzyl)sulphonamide (compound 64)

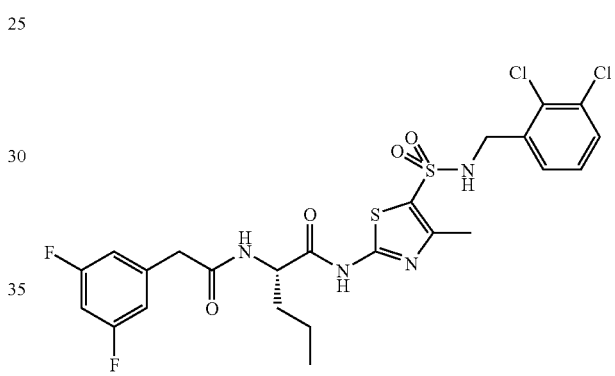

Example 6.1

2-acetamido-4-methylthiazole 5-(N-2,3-dichlorobenzyl)sulphonamide

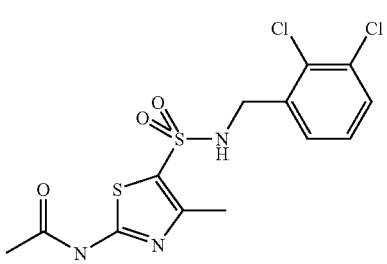

2.5 g of commercial 2-acetamido-4-methylthiazole-5-sulphonyl chloride in 60 ml of anhydrous dichloromethane, at 0° C., are admixed with 2 equivalents (3.5 g) of 2,3-dichlorobenzylamine. The mixture is allowed to return to ambient temperature. After approximately 5 h it is extracted with dichloromethane and washed twice with a 1 M solution of sodium hydrogen sulphate and then twice with saturated sodium bicarbonate solution. The organic phase is washed with saturated sodium chloride solution and then dried over anhydrous magnesium sulphate. Filtration, evaporation and solidification in a dichloromethane/pentane mixture give 2.9 g (95%) of a white powder.

NMR 300 MHz (DMSO) δ ppm: 2.16 (s, 3H); 2.40 (s, 3H); 4.21 (s, 2H); 7.28-7.56 (m, 3H).

Example 6.2

2-amino-4-methylthiazole 5-(N-2,3-dichlorobenzyl)sulphonamide

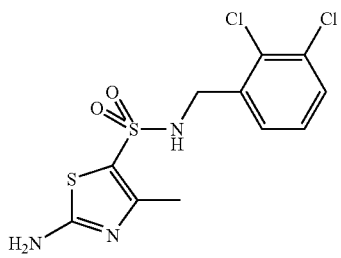

2.4 g of 2-acetamido-4-methylthiazole 5-(N-2,3-dichlorobenzyl)sulphonamide, obtained in step 6.1, in 100 ml of a 2 N HCl solution are heated at 100° C. for 6 h. The contents of the round-bottomed flask are evaporated and then the residue is taken up in dichloromethane. It is washed three times with 20% sodium carbonate solution and the organic phase is dried over anhydrous magnesium sulphate. Filtration and evaporation give 2 g of white powder.

NMR 300 MHz (DMSO) δ ppm: 2.24 (s, 3H); 4.02 (d, 2H); 7.31-7.60 (m, 3H); 7.69 (s, 2H); 8.28 (t, 1H).

Example 6.3

2-{2-(S)-[2-(3,5-difluorophenyl)acetylamino]pentanoyl}amino-4-methylthiazole 5-(N-2,3-dichlorobenzyl)sulphonamide Starting from the 2-amino-4-methylthiazole 5-(N-2,3-dichlorobenzyl)sulphonamide obtained in step 6.2, 2 successive couplings are carried out according to the processes described in steps 1.4 and 1.5 of Example 1.

This gives 0.42 g of end product.

NMR: described in the table below. (compound 64)

LC/MS: $MH^+=605$.

The table which follows illustrates the chemical structures and physical properties of some examples of compounds according to the invention.

TABLE 1

| Cpd | $R_1$ | $R_2, R'_2$ | $R_3$ | $R_4$ |
|---|---|---|---|---|
| 1. | 3,5-difluorophenyl | OH, H (S) | —(CH$_2$)$_2$CH$_3$ (S) | 5-methyl-3-methyl-1,2,4-oxadiazole |
| 2. | 3,5-difluorophenyl | OH, H | —(CH$_2$)$_2$CH$_3$ (S) | 5-methyl-3-methyl-1,2,4-oxadiazole |
| 3. | 3,5-difluorophenyl | OH, H (S) | —(CH$_2$)$_2$CH$_3$ (S) | 5-methyl-3-methyl-1,2,4-oxadiazole |
| 4. | 3,5-difluorophenyl | OH, H (R) | —(CH$_2$)$_2$CH$_3$ (S) | 5-methyl-3-methyl-1,2,4-oxadiazole |
| 5. | 3,5-difluorophenyl | OH, H (S) | —(CH$_2$)$_2$CH$_3$ (S) | 5-methyl-3-phenyl-1,2,4-oxadiazole |

TABLE 1-continued

| # | R1 | R2, R3 | R4 | Ar |
|---|---|---|---|---|
| 6. | 3,5-difluorophenyl | OH, H (R) | —(CH₂)₂CH₃ (S) | 5-methyl-3-phenyl-1,2,4-oxadiazole |
| 7. | —C(CH₃)₃ | OH, H (S) | —(CH₂)₂CH₃ (S) | 5-methyl-3-phenyl-1,2,4-oxadiazole |
| 8. | —CH(CH₃)₂ | OH, H (S) | —(CH₂)₂CH₃ (S) | 5-methyl-3-phenyl-1,2,4-oxadiazole |
| 9. | 3,5-difluorophenyl | H, H | —(CH₂)₂CH₃ (S) | —CN |
| 10. | —C(CH₃)₃ | OH, H (S) | —(CH₂)₂CH₃ (S) | 5-methyl-3-methyl-1,2,4-oxadiazole |
| 11. | —C(CH₃)₃ | OH, H (S) | —(CH₂)₂CH₃ (S) | 3-methyl-5-methyl-1,2,4-oxadiazole (isomer) |
| 12. | —C(CH₃)₃ | OH, H (S) | —(CH₂)₂CH₃ (S) | 5-methyl-3-methyl-1,2,4-oxadiazole |
| 13. | —C(CH₃)₃ | OH, H (S) | —(CH₂)₂CH₃ (S) | 3-methyl-5-methyl-1,2,4-oxadiazole |
| 14. | —C(CH₃)₃ | OH, H (S) | —(CH₂)₂CH₃ (S) | 5-methyl-3-methyl-1,2,4-oxadiazole |
| 15. | —C(CH₃)₃ | OH, H (S) | —(CH₂)₂CH₃ (S) | 5-methyl-3-methyl-1,2,4-oxadiazole |
| 16. | —C(CH₃)₃ | OH, H (S) | —(CH₂)₂CH₃ (S) | 5-methyl-3-methyl-1,2,4-oxadiazole |

TABLE 1-continued

| | | | | |
|---|---|---|---|---|
| 17. | —C(CH₃)₃ | OH, H (S) | —(CH₂)₂CH₃ (S) | —CN |
| 18. | 3,5-difluorophenyl | OH, H | —(CH₂)₂CH₃ (S) | —CN |
| 19. | 3,5-difluorophenyl | H, H | —(CH₂)₂CH₃ (S) | 3-methyl-1,2,4-oxadiazol-5-yl (5-methyl, 3-CH₃ isomer) |
| 20. | —C(CH₃)₃ | OH, H (S) | —(CH₂)₂CH₃ (S) | 3-methyl-1,2,4-oxadiazol-5-yl |
| 21. | —C(CH₃)₃ | OH, H (S) | —(CH₂)₂CH₃ (S) | 3-methyl-1,2,4-oxadiazol-5-yl |
| 22. | —C(CH₃)₃ | OH, H (S) | —(CH₂)₂CH₃ (S) | —CN |
| 23. | —C(CH₃)₃ | OH, H (S) | —(CH₂)₂CH₃ (S) | —CN |
| 24. | —C(CH₃)₃ | OH, H (S) | —(CH₂)₂CH₃ (S) | 3-methyl-1,2,4-oxadiazol-5-yl |
| 25. | 3,5-difluorophenyl | OH, H (S) | —(CH₂)₂CH₃ (S) | 3-methyl-1,2,4-oxadiazol-5-yl |
| 26. | 3,5-difluorophenyl | OH, H (S) | —(CH₂)₂CH₃ (S) | 5-methyl-1,2,4-oxadiazol-3-yl |
| 27. | 3,5-difluorophenyl | OH, H (R) | —(CH₂)₂CH₃ (S) | 5-methyl-1,2,4-oxadiazol-3-yl |
| 28. | —C(CH₃)₃ | OH, H (S) | —(CH₂)₂CH₃ (S) | 5-methyl-1,2,4-oxadiazol-3-yl |
| 29. | 3,5-difluorophenyl | OH, H (S) | —(CH₂)₂CH₃ (S) | —CN |
| 30. | 3,5-difluorophenyl | OH, H (S) | —(CH₂)₂CH₃ (S) | —CN |
| 31. | 3,5-difluorophenyl | OH, H (S) | —(CH₂)₂CH₃ (S) | 5-methyl-1,2,4-oxadiazol-3-yl |

TABLE 1-continued

| | | | | |
|---|---|---|---|---|
| 32. | 3,5-difluorophenyl | H, H | —(CH$_2$)$_2$CH$_3$ (S) | 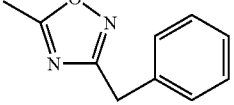 |
| 33. | —C(CH$_3$)$_3$ | OH, H (S) | —(CH$_2$)$_2$CH$_3$ (S) | 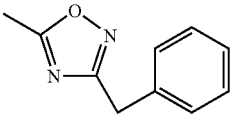 |
| 34. | —C(CH$_3$)$_3$ | OH, H (S) | —(CH$_2$)$_2$CH$_3$ (S) | 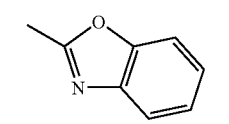 |
| 35. | 3,5-difluorophenyl | H, H | —(CH$_2$)$_2$CH$_3$ (S) | 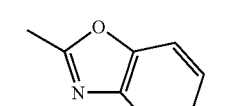 |
| 36. | —C(CH$_3$)$_3$ | OH, H (S) | —(CH$_2$)$_2$CH$_3$ (S) | 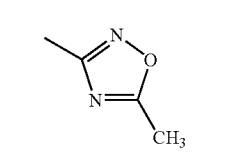 |
| 37. | 3,5-difluorophenyl | H, H | —(CH$_2$)$_2$CH$_3$ (S) | 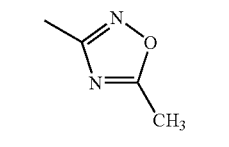 |
| 38. | 3,5-difluorophenyl | OH, H (S) | —(CH$_2$)$_2$CH$_3$ (S) | 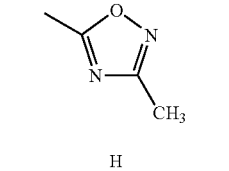 |
| 39. | 3,5-difluorophenyl | OH, H | —(CH$_2$)$_2$CH$_3$ (S) | H |
| 40. | 3,5-difluorophenyl | OH, H | —(CH$_2$)$_2$CH$_3$ (S) | CH$_3$ |
| 41. | —C(CH$_3$)$_3$ | OH, H (S) | —(CH$_2$)$_2$CH$_3$ (S) | H |
| 42. | —CH(CH$_3$)$_2$ | OH, H (S) | —(CH$_2$)$_2$CH$_3$ (S) | H |
| 43. | 3,5-difluorophenyl | OH, H (S) | —(CH$_2$)$_2$CH$_3$ (S) | H |
| 44. | —C(CH$_3$)$_3$ | OH, H (S) | —(CH$_2$)$_2$CH$_3$ (S) | CH$_3$ |
| 45. | 3,5-difluorophenyl | H, H | —(CH$_2$)$_2$CH$_3$ (S) | CH$_3$ |
| 46. | —C(CH$_3$)$_3$ | OH, H (S) | —(CH$_2$)$_2$CH$_3$ (S) | CH$_3$ |
| 47. | —C(CH$_3$)$_3$ | OH, H (S) | —(CH$_2$)$_2$CH$_3$ (S) | H |
| 48. | —C(CH$_3$)$_3$ | OH, H (S) | —(CH$_2$)$_2$CH$_3$ (S) | H |
| 49. | 3,5-difluorophenyl | OH, H (S) | —(CH$_2$)$_2$CH$_3$ (S) | H |
| 50. | 3,5-difluorophenyl | OH, H (R) | —(CH$_2$)$_2$CH$_3$ (S) | H |
| 51. | —C(CH$_3$)$_3$ | OH, H (S) | —(CH$_2$)$_2$CH$_3$ (S) | H |
| 52. | 3,5-difluorophenyl | H, H | —(CH$_2$)$_2$CH$_3$ (S) | CH$_3$ |
| 53. | 3,5-difluorophenyl | H, H | —(CH$_2$)$_2$CH$_3$ (S) | H |
| 54. | 3,5-difluorophenyl | OH, H | —(CH$_2$)$_2$CH$_3$ (S) | H |

TABLE 1-continued

| | | | | |
|---|---|---|---|---|
| 55. | —C(CH₃)₃ | OH, H (S) | —(CH₂)₂CH₃ (S) | CH₃ |
| 56. | —C(CH₃)₃ | OH, H (S) | —(CH₂)₂CH₃ (S) | CH₃ |
| 57. | 3,5-difluorophenyl | H, H | —(CH₂)₂CH₃ (S) | CH₃ |
| 58. | 3,5-difluorophenyl | H, H | —(CH₂)₂CH₃ (S) | CH₃ |
| 59. | —C(CH₃)₃ | OH, H (S) | —(CH₂)₂CH₃ (S) | CH₃ |
| 60. | 3,5-difluorophenyl | H, H | CH₃(CH₂)₂— (S) | H |
| 61. | —C(CH₃)₃ | OH, H (S) | —(CH₂)₂CH₃ (S) | CH₃ |
| 62. | 3,5-difluorophenyl | OH, H (S) | —(CH₂)₂CH₃ (S) | CH₃ |
| 63. | 3,5-difluorophenyl | H, H | CH₃(CH₂)₂— (S) | CH₃ |
| 64. | 3,5-difluorophenyl | H, H | CH₃(CH₂)₂— (S) | CH₃ |
| 65. | —C(CH₃)₃ | OH, H (S) | CH₃(CH₂)₂— (S) | H |
| 66. | —C(CH₃)₃ | OH, H (S) | CH₃(CH₂)₂— (S) | CH₃ |
| 67. | 3,5-difluorophenyl | OH, H (S) | CH₃(CH₂)₂— (S) | H |
| 68. | 3,5-difluorophenyl | OH, H (R) | CH₃(CH₂)₂— (S) | H |
| 69. | 3,5-difluorophenyl | OH, H (S) | CH₃(CH₂)₂— (S) | CH₃ |
| 70. | 3,5-difluorophenyl | OH, H (R) | CH₃(CH₂)₂— (S) | CH₃ |
| 71. | 3,5-difluorophenyl | H, H | CH₃(CH₂)₂— (S) | CH₃ |
| 72. | 3,5-difluorophenyl | H, H | CH₃(CH₂)₂— (S) | CH₃ |
| 73. | —C(CH₃)₃ | OH, H (S) | CH₃(CH₂)₂— (S) | CH₃ |
| 74. | 3,5-difluorophenyl | H, H | CH₃(CH₂)₂— (S) | CH₃ |
| 75. | —C(CH₃)₃ | OH, H (S) | CH₃(CH₂)₂— (S) | CH₃ |
| 76. | —CH(CH₃)₂ | OH, H (S) | CH₃(CH₂)₂— (S) | CH₃ |
| 77. | —C(CH₃)₃ | OH, H (S) | CH₃(CH₂)₂— (S) | CH₃ |
| 78. | 3,5-difluorophenyl | H, H | CH₃(CH₂)₂— (S) | CH₃ |
| 79. | —CH(CH₃)₂ | OH, H (S) | CH₃(CH₂)₂— (S) | CH₃ |
| 80. | —C(CH₃)₃ | OH, H (S) | CH₃(CH₂)₂— (S) | CH₃ |
| 81. | —C(CH₃)₃ | OH, H (S) | —(CH₂)₂CH₃ (S) | 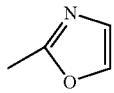 |
| 82. | 3,5-difluorophenyl | H, H | —(CH₂)₂CH₃ (S) | 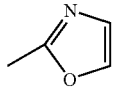 |
| 83. | —C(CH₃)₃ | OH, H (S) | —(CH₂)₂CH₃ (S) | 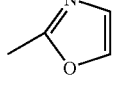 |
| 84. | 3,5-difluorophenyl | H, H | —(CH₂)₂CH₃ (S) | 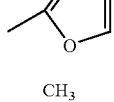 |
| 85. | 3,5-difluorophenyl | H, H | —CH₂CH₃ (S) | CH₃ |
| 86. | —C(CH₃)₃ | OH, H (S) | —CH₂CH₃ (S) | CH₃ |
| 87. | —CH(CH₃)₂ | OH, H (S) | —CH₂CH₃ (S) | CH₃ |

TABLE 1-continued

| | | | | |
|---|---|---|---|---|
| 88. | 3,5-difluorophenyl | H, H | —CH₃ (S) | CH₃ |
| 89. | —C(CH₃)₃ | OH, H (S) | —CH₃ (S) | CH₃ |
| 90. | —CH(CH₃)₂ | OH, H (S) | —CH₃ (S) | CH₃ |
| 91. | —C(CH₃)₃ | OH, H (S) | —(CH₂)₂CH₃ (S) | CH₃ |
| 92. | 3,5-difluorophenyl | H, H | —(CH₂)₂CH₃ (S) | CH₃ |
| 93. | 3,5-difluorophenyl | OH, H | —(CH₂)₂CH₃ (S) | CH₃ |
| 94. | 3,5-difluorophenyl | H, H | —(CH₂)₂CH₃ (S) | CH₃ |
| 95. | 3,5-difluorophenyl | H, H | —(CH₂)₂CH₃ (S) | CH₃ |
| 96. | —C(CH₃)₃ | OH, H (S) | —(CH₂)₂CH₃ (S) | CH₃ |
| 97. | —C(CH₃)₃ | OH, H (S) | —(CH₂)₂CH₃ (S) | CH₃ |
| 98. | 3,5-difluorophenyl | OH, H (S) | —(CH₂)₂CH₃ (S) | CH₃ |
| 99. | 3,5-difluorophenyl | OH, H (R) | —(CH₂)₂CH₃ (S) | CH₃ |
| 100. | —CH(CH₃)₂ | OH, H (S) | —(CH₂)₂CH₃ (S) | CH₃ |
| 101. | —C(CH₃)₃ | OH, H (S) | —(CH₂)₂CH₃ (S) | CH₃ |
| 102. | 3,5-difluorophenyl | H, H | —(CH₂)₂CH₃ (S) | CH₃ |
| 103. | 3,5-difluorophenyl | OH, H | —(CH₂)₂CH₃ (S) | CH₃ |
| 104. | —C(CH₃)₃ | OH, H (S) | —(CH₂)₂CH₃ (S) | CH₃ |
| 105. | 3,5-difluorophenyl | H, H | —(CH₂)₂CH₃ (S) | CH₃ |
| 106. | 3,5-difluorophenyl | OH, H | —(CH₂)₂CH₃ (S) | CH₃ |
| 107. | —C(CH₃)₃ | OH, H (S) | —(CH₂)₂CH₃ (S) | CH₃ |
| 108. | 3,5-difluorophenyl | H, H | —(CH₂)₂CH₃ (S) | CH₃ |
| 109. | —C(CH₃)₃ | OH, H (S) | —(CH₂)₂CH₃ (S) | CH₃ |
| 110. | 3,5-difluorophenyl | H, H | —(CH₂)₂CH₃ (S) | CH₃ |
| 111. | 3,5-difluorophenyl | OH, H (S) | —(CH₂)₂CH₃ (S) | CH₃ |
| 112. | 3,5-difluorophenyl | OH, H (R) | —(CH₂)₂CH₃ (S) | CH₃ |
| 113. | —C(CH₃)₃ | OH, H (S) | —(CH₂)₂CH₃ (S) | CH₃ |
| 114. | 3,5-difluorophenyl | H, H | —(CH₂)₂CH₃ (S) | CH₃ |
| 115. | 3,5-difluorophenyl | OH, H (S) | —(CH₂)₂CH₃ (S) | CH₃ |
| 116. | 3,5-difluorophenyl | OH, H (R) | —(CH₂)₂CH₃ (S) | CH₃ |
| 117. | 3,5-difluorophenyl | OH, H (S) | —(CH₂)₂CH₃ (S) | CH₃ |
| 118. | 3,5-difluorophenyl | OH, H (R) | —(CH₂)₂CH₃ (S) | CH₃ |
| 119. | —C(CH₃)₃ | OH, H (S) | —(CH₂)₂CH₃ (S) | CH₃ |
| 120. | —C(CH₃)₃ | OH, H (S) | —(CH₂)₂CH₃ (S) | CH₃ |
| 121. | 3,5-difluorophenyl | H, H | —(CH₂)₂CH₃ (S) | CH₃ |
| 122. | 3,5-difluorophenyl | H, H | —(CH₂)₂CH₃ (S) | CH₃ |
| 123. | 3,5-difluorophenyl | OH, H (S) | —(CH₂)₂CH₃ (S) | CH₃ |
| 124. | 3,5-difluorophenyl | OH, H | —(CH₂)₂CH₃ (S) | CH₃ |
| 125. | —C(CH₃)₃ | OH, H (S) | —(CH₂)₂CH₃ (S) | 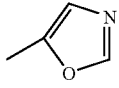 |

TABLE 1-continued
| | | | | |
|---|---|---|---|---|
| 126. | —CH(CH$_3$)$_2$ | OH, H (S) | —(CH$_2$)$_2$CH$_3$ (S) | 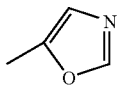 |
| 127. | 3,5-difluorophenyl | H, H | —(CH$_2$)$_2$CH$_3$ (S) | 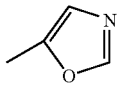 |
| 128. | —C(CH$_3$)$_3$ | OH, H (S) | —(CH$_2$)$_2$CH$_3$ (S) | 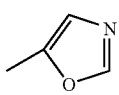 |
| 129. | —C(CH$_3$)$_3$ | OH, H (S) | —(CH$_2$)$_2$CH$_3$ (S) | 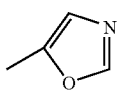 |
| 130. | 3,5-difluorophenyl | H, H | —(CH$_2$)$_2$CH$_3$ (S) | 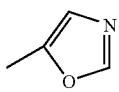 |
| 131. | —C(CH$_3$)$_3$ | OH, H (S) | —(CH$_2$)$_2$CH$_3$ (S) | 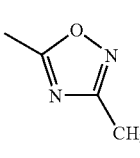 |
| 132. | —CH(CH$_3$)$_2$ | OH, H (S) | —(CH$_2$)$_2$CH$_3$ (S) | 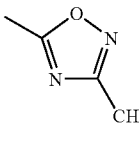 |
| 133. | —C(CH$_3$)$_3$ | OH, H (S) | —(CH$_2$)$_2$CH$_3$ (S) | 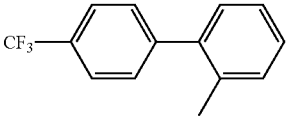 |
| 134. | —CH(CH$_3$)$_2$ | OH, H (S) | —(CH$_2$)$_2$CH$_3$ (S) | 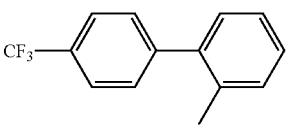 |
| 135. | 3,5-difluorophenyl | H, H | —(CH$_2$)$_2$CH$_3$ (S) | 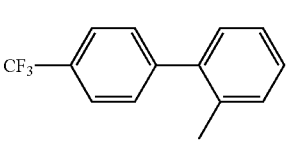 |
| 136. | —CH(CH$_3$)$_2$ | OH, H (S) | —(CH$_2$)$_2$CH$_3$ (S) | 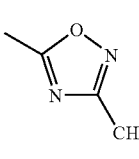 |
| 137. | —CH(CH$_3$)$_2$ | OH, H (S) | —(CH$_2$)$_2$CH$_3$ (S) | 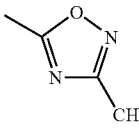 |

TABLE 1-continued

| Cpd | R₅ | NMR (DMSO d6 unless specified) |
|---|---|---|
| 1. | —CH(CH₃)₂ | 0.89 (t, 3H); 1.26-1.36 (m, 2H); 1.39 (d, 6H); 1.78 (m, 2H); 2.48 (s, 3H); 4.21 (m, 1H); 4.53 (m, 1H); 5.13 (d, 1H); 6.63 (d, 1H); 7.20 (m, 3H); 8.34 (d, 1H); 12.68 (s, 1H)*** |
| 2. | —CH(CH₃)₂ | 0.84-0.90 (2 t, 3H); 1.25-1.35 (m, 2H); 1.35 (d, 6H); 1.76 (m, 2H); 2.45 (s, 3H); 4.17 (m, 1H); 4.48 (m, 1H); 5.11 and 5.13 (2 a, 1H); 6.48 and 6.60 (2 d, 1H); 7.14-7.23 (m, 3H); 8.32 and 8.35 (2 d, 1H); 12.69 (s, broad, 1H)*** |
| 3. | 2-methylphenyl-O-CH₂-phenyl | 0.88 (t, 3H); 1.24-1.34 (m, 2H); 1.79 (m, 2H); 2.31 (s, 3H); 4.58 (m, 1H); 5.09 (s, 2H); 5.13 (m, 1H); 6.63 (d, 1H); 7.09-7.50 (m, 12H); 8.37 (d, 1H); 12.79 (s, broad, 1H)*** |
| 4. | 2-methylphenyl-O-CH₂-phenyl | 0.90 (t, 3H); 1.27-1.40 (m, 2H); 1.78 (m, 2H); 2.30 (s, 3H); 4.52 (m, 1H, broad); 5.07 (s, 2H); 5.15 (d, 1H); 6.48 (d, 1H); 7.00-7.50 (m, 12H); 8.40 (d, 1H); 12.85 (s, 1H, broad)*** |
| 5. | —CH(CH₃)₂ | 0.91 (t, 3H); 1.21-1.39 (m, 2H); 1.47 (d, 6H); 1.81 (m, 2H); 4.32 (m, 1H); 4.56 (m, 1H); 5.16 (d, 1H); 6.65 (d, 1H); 7.22 (m, 3H); 7.68 (m, 3H); 8.16 (m, 2H); 8.37 (d, 1H); 12.76 (s, 1H, broad)*** |
| 6. | —CH(CH₃)₂ | 0.92 (t, 3H); 1.28-1.41 (m, 2H); 1.43 (d, 6H); 1.80 (m, 2H); 4.31 (m, 1H); 4.52 (m, 1H); 5.17 (d, 1H); 6.52 (d, 1H); 7.19 (m, 3H); 7.68 (m, 3H); 8.15 (m, 2H); 8.40 (d, 1H); 12.80 (s, 1H, broad)*** |
| 7. | —CH(CH₃)₂ | 0.93 (t, 3H); 0.97 (s, 9H); 1.31-1.42 (m, 2H); 1.44 (m, 6H); 1.77 (m, 2H); 3.62 (d, 1H); 4.30 (m, 1H); 4.60 (m, 1H); 5.62 (d, 1H); 7.66 (m, 3H); 7.88 (d, 1H); 8.13 (m, 2H); 12.71 (s, 1H, broad)*** |
| 8. | —CH(CH₃)₂ | 0.85 (d, 3H); 0.94 (t, 3H); 0.98 (d, 3H); 1.20-1.50 (m, 8H); 1.78 (m, 2H); 2.05 (m, 1H); 3.80 (m, 1H); 4.30 (m, 1H); 4.61 (m, 1H); 5.54 (d, 1H); 7.66 (m, 3H); 7.94 (d, 1H); 8.14 (m, 2H); 12.75 (s, 1H, broad)*** |
| 9. | —CH(CH₃)₂ | 0.95 (t, 3H); 1.36-1.45 (m, 8H); 1.69-1.75 (m, 2H); 3.43 (m, 1H); 3.64 (d, 2H); 4.49 (m, 1H); 7.00-7.20 (m, 3H); 8.61 (d, 1H); 12.69 (s, 1H)*** |
| 10. | 2-methylbiphenyl | 0.87 (t, 3H); 0.90 (s, 9H); 1.23-1.28 (m, 2H); 1.70 (m, 2H); 2.30 (s, 3H); 3.56 (d, 1H); 4.54 (s, broad, 1H); 5.61 (d, 1H); 7.04 (d, 2H); 7.18 (m, 3H); 7.43-7.60 (m, 4H); 7.83 (d, 1H); 12.63 (s, broad, 1H)*** |
| 11. | —CH(CH₃)₂ | 0.96 (t, 3H); 1.01 (s, 9H); 1.36-1.45 (m, 8H); 1.79 (m, 2H); 2.75 (s, 3H); 3.65 (d, 1H); 4.15 (m, 1H); 4.62 (m, 1H); 5.67 (d, 1H); 7.90 (d, 1H); 12.56 (s, 1H, broad)*** |

TABLE 1-continued
| | | |
|---|---|---|
| 12. | 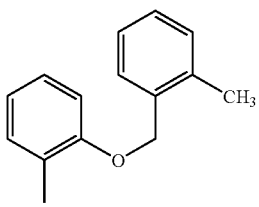 | 0.88 (t, 3H); 0.91 (s, 9H); 1.23-1.35 (m, 2H); 1.73 (m, 2H); 2.13 (s, 3H); 2.23 (s, 3H); 3.57 (d, 1H); 4.57 (d, broad, 1H); 5.02 (s, 2H); 5.58 (d, 1H); 7.04-7.50 (m, 8H); 8.41 (d, 1H); 12.68 (s, broad, 1H)*** |
| 13. | 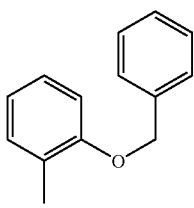 | 0.98 (t, 3H); 1.03 (s, 9H); 1.39-1.50 (m, 2H); 1.84 (m, 2H); 2.60 (s, 3H); 3.68 (d, 1H); 4.69 (m, 1H); 5.16 (s, 2H); 5.72 (d, 1H); 7.00-7.60 (m, 9H); 7.95 (d, 1H); 12.71 (s, 1H)*** |
| 14. | 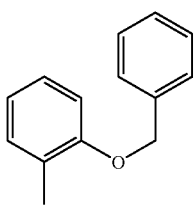 | 0.93 (t, 3H); 0.98 (s, 9H); 1.33-1.47 (m, 2H); 1.80 (m, 2H); 2.32 (s, 3H); 3.63 (d, 1H); 4.63 (m, 1H); 5.12 (s, 2H); 5.65 (d, 1H); 7.00-7.52 (m, 9H); 7.91 (d, 1H); 12.87 (s, 1H, broad)*** |
| 15. | 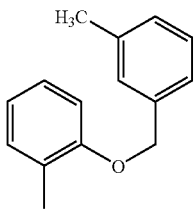 | 0.88 (t, 3H); 0.91 (s, 9H); 1.28-1.36 (m, 2H); 1.73 (m, 2H); 2.22 (s, 3H); 2.26 (s, 3H); 3.57 (d, 1H); 4.57 (d, 1H); 4.99 (s, 2H); 5.59 (d, (1H); 6.91 (m, 2H); 7.06 (m, 2H); 7.13 (m, 1H); 7.16 (m, 1H); 7.39-7.44 (m, 2H); 7.90 (m, 2H); 12.71 (s, broad, 1H)*** |
| 16. | 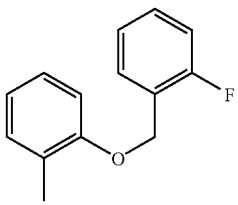 | 0.97 (t, 3H); 0.99 (s, 9H); 1.34-1.42 (m, 2H); 1.70 (m, 2H); 2.32 (s, 3H); 3.65 (d, 1H); 4.65 (d, 1H); 5.15 (s, 2H); 5.67 (d, 1H); 7.10-7.55 (m, 8H); 7.93 (d, 1H); 12.74 (s, broad, 1H)*** |
| 17. | —CH(CH$_3$)$_2$ | 0.94 (t, 3H); 0.98 (s, 9H); 1.32-1.39 (m, 2H); 1.42 (d, 6H); 1.76 (m, 2H); 3.43 (m, 1H); 3.64 (d, 1H); 4.60 (m, 1H); 5.61 (d, 1H); 7.60 (d, 1H); 12.60 (s, 1H, broad)*** |
| 18. | —CH(CH$_3$)$_2$ | 0.90 (m, 3H); 1.28-1.39 (m, 2H); 1.40 (m, 6H); 3.44 (m, 1H); 4.53 (m, 1H); 5.16 (2 d, 1H); 6.49 and 6.61 (2 d, 1H); 7.19-7.34 (m, 3H); 8.37 and 8.41 (2 d, 1H); 12.65 and 12.70 (2 d, 1H, broad)*** |
| 19. | 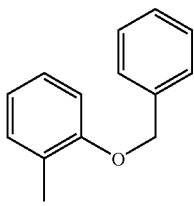 | 0.98 (t, 3H); 1.39-1.83 (2 m, 4H); 2.35 (s, 3H); 3.67 (m, 1H); 4.57 (m, 1H); 5.13 (s, 2H); 7.02-7.54 (m, 12H); 8.65 (d, 1H); 12.9 (s, 1H)*** |

TABLE 1-continued
| | | |
|---|---|---|
| 20. | 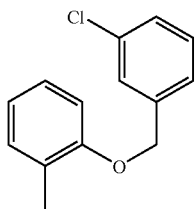 | 0.97 (t, 3H); 1.01 (s, 9H); 1.39-1.47 (m, 2H); 1.81 (m, 2H); 2.35 (s, 3H); 3.66 (d, 1H); 4.67 (d, broad, 1H); 5.15 (s, 2H); 5.71 (d, 1H); 7.15-7.55 (m, 8H); 7.97 (d, 1H); 12.86 (s, broad, 1H)*** |
| 21. | 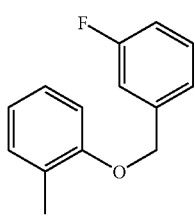 | 0.95 (t, 3H); 0.99 (s, 9H); 1.33-1.44 (m, 2H); 1.80 (m, 2H); 2.33 (s, 3H); 3.65 (d, 1H); 4.65 (s, broad, 1H); 5.10 (s, 2H); 5.70 (d, 1H); 6.96-7.53 (m, 8H); 7.96 (d, 1H); 12.88 (s, broad, 1H)*** |
| 22. | 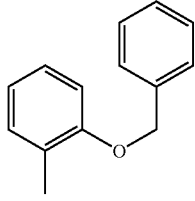 | 0.94 (t, 3H); 1.04 (s, 9H); 1.31-1.44 (m, 2H); 1.77 (m, 2H); 3.63 (d, 1H); 4.62 (m, 1H); 5.33 (s, 2H); 5.62 (d, 1H); 7.15-7.95 (m, 10H); 12.70 (s, 1H, broad)*** |
| 23. | 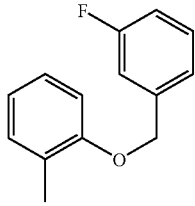 | 0.94 (t, 3H); 0.98 (s, 9H); 1.30-1.44 (m, 2H); 1.77 (m, 2H); 3.63 (d, 1H); 4.62 (m, 1H); 5.35 (s, 2H); 5.62 (d, 1H); 7.18-7.95 (m, 9H); 12.72 (s, 1H, broad)*** |
| 24. | 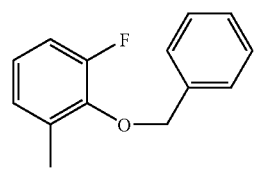 | 0.87 (t, 3H); 0.89 (s, 3H); 1.28-1.35 (m, 2H); 1.75 (m, 2H); 2.25 (s, 3H); 3.57 (d, 1H); 4.59 (m, 1H); 4.86 (s, 2H); 5.57 (d, 1H); 6.98 (d, 1H); 7.15-7.42 (m, 7H); 7.86 (d, 1H); 12.75 (s, broad, 1H)*** |
| 25. | 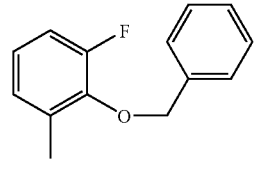 | 0.85 (t, 3H); 1.21-1.33 (m, 2H); 1.75 (m, 2H); 2.48 (s, 3H); 4.51 (m, 1H); 4.86 (s, 2H); 5.08 (d, 1H); 6.55 (d, 1H); 6.97-7.43 (m, 13H); 8.32 (d, 1H); 12.80 (s, 1H)*** |
| 26. | 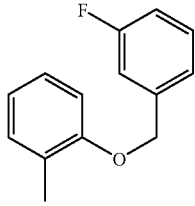 | 0.84 (t, 3H); 1.21-1.31 (m, 2H ); 1.74 (m, 2H); 2.48 (s, 3H); 4.52 (m, 1H); 5.00-5.10 (m, 3H); 6.58 (d, 1H); 6.96-7.40 (m, 11H); 8.30 (d, 1H); 12.68 (s, 1H)*** |

TABLE 1-continued
| | | |
|---|---|---|
| 27. | 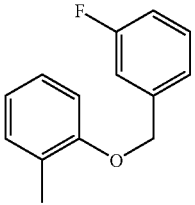 | 0.85 (t, 3H); 1.25-1.35 (m, 2H); 1.73 (m, 2H); 2.48 (s, 3H); 4.50 (m, 1H); 5.07 (s, 2H) 5.11 (d, 1H); 6.43 (d, 1H); 6.90-7.40 (m, 11H); 8.35 (d, 1H); 12.73 (s, 1H)*** |
| 28. | 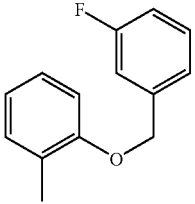 | 0.89 (t, 3H); 1.32 (m, 2H); 1.73 (m, 2H); 2.48 (s, 3H); 3.56 (d, 1H); 5.07 (s, 2H); 5.61 (d, 1H); 6.90-7.40 (m, 8H); 7.84 (d, 1H); 12.63 (s, 1H)*** |
| 29. | —CH(CH$_3$)$_2$ | 0.82 (t, 3H); 1.20-1.27 (m, 2H); 1.33 (d, 6H); 1.70 (m, 2H); 3.35 (m, 1H); 4.47 (m, 1H); 5.07 (d, 1H); 6.54 (d, 1H); 7.15 (m, 3H); 8.29 (d, 1H); 12.57 (s, 1H)*** |
| 30. | 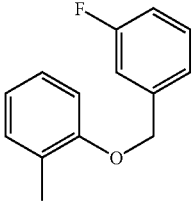 | 0.83 (t, 3H); 1.20-1.30 (m, 2H); 1.73 (m, 2H); 4.51 (m, 1H); 5.08 (d, 1H); 5.29 (s, 2H); 6.56 (d, 1H); 7.12-7.68 (m, 11H); 8.33 (d, 1H); 12.71 (s, 1H)*** |
| 31. | 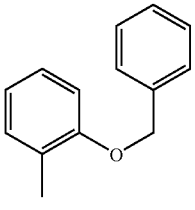 | 0.84 (t, 3H); 1.25 (m, 2H); 1.75 (m, 2H); 4.51 (d, 1H); 5.05 (s, 2H); 5.08 (d, 1H); 6.58 (d, 1H); 6.90-7.40 (m, 12H); 8.31 (d, 1H); 12.65 (s, 1H)*** |
| 32. | H | 0.88 (t, 3H); 1.28-1.37 (m, 2H); 1.65.(m, 2H); 3.57 (m, 2H); 4.15 (s, 2H); 4.45 (m, 1H); 6.98 (d, 2H); 7.07 (t, 1H); 7.25 (t, 1H); 7.34 (s, 4H); 8.26 (s, 1H); 8.54 (d, 1H); 12.82 (s broad, 1H)**** |
| 33. | H | 0.85 (t, 3H); 0.91 (s, 9H); 1.24 and 1.35 (2 m, 2H); 1.72 (m, 2H); 3.56 (d, 1H); 4.16 (s, 2H); 4.56 (m, 1H); 5.61 (d, 1H); 7.26-7.35 (m, 5H); 7.84 (d, 1H); 8.28 (s, 1H); 12.72 (s broad, 1H)**** |
| 34. | —CH(CH$_3$)$_2$ | 0.88 (t, 3H); 0.92 (s, 9H); 1.28-1.35 (m, 2H); 1.36 (d, 6H); 1.72 (m, 2H); 3.57 (d, 1H); 4.35 (m, 1H); 4.55 (m, 1H); 5.60 (d, 1H); 7.43 (m, 2H); 7.77 (d, 1H); 7.82 (m, 2H); 12.60 (s, 1H)*** |
| 35. | —CH(CH$_3$)$_2$ | 0.88 (t, 3H); 1.31 (m, 2H); 1.37 (d, 6H); 1.67 (m, 2H); 3.57 (m, 2H); 4.35 (m, 1H); 4.43 (m, 1H); 6.98-7.10 (m, 3H); 7.42 (m, 2H); 7.75-7.83 (m, 2H); 8.53 (d, 1H); 12.64 (s, 1H)*** |
| 36. | 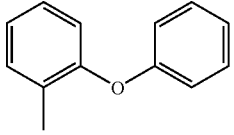 | 0.87 (t, 3H); 0.91 (s, 9H); 1.25-1.75 (m, 4H); 2.50 (s, 3H); 3.55 (d, 1H); 4.55 (m, 1H); 5.61 (d, 1H); 6.81 (d, 2H); 6.93 (d, 1H); 7.06 (t, 1H); 7.21 (t, 1H); 7.30 (m, 2H); 7.46 (m, 2H); 7.82 (d, 1H); 12.64 (s, 1H)*** |

TABLE 1-continued

| # | Structure | NMR Data |
|---|---|---|
| 37. | (2-methylphenoxy)benzene | 0.87 (t, 3H); 1.25-1.75 (m, 4H); 2.50 (s, 3H); 3.56 (m, 2H); 4.44 (m, 1H); 6.80-7.50 (m, 12H); 8.53 (d, 1H); 12.73 (s, 1H)*** |
| 38. | 1-fluoro-4-((2-methylphenoxy)methyl)benzene | 0.83 (t, 3H); 1.22-1.30 (m, 2H); 1.74 (m, 2H); 2.25 (s, 3H); 4.51 (m, 1H); 5.01 (s, 1H); 5.08 (d, 1H); 6.57 (d, 1H); 7.05-7.21 (m, 9H); 7.40-7.45 (m, 2H); 8.32 (d, 1H); 12.75 (s broad, 1H)*** |
| 39. | 3-methyl-5-methyl-1,2,4-oxadiazole | 0.88 and 0.89 (2 t, 3H); 1.29 (m, 2H); 1.78 (m, 2H); 2.43 (s, 3H); 4.58 (m, 1H); 5.14 (m, 1H); 6.47 and 6.61 (2 d, 1H); 7.13 (m, 3H); 8.43 (s, 1H); 8.39-8.47 (m, 3H); 12.99 (s, broad, 1H)*** |
| 40. | 3-methyl-5-methyl-1,2,4-oxadiazole | 0.88 and 0.90 (2 t, 3H); 1.31 (m, 2H); 1.79 (m, 2H); 2.43 and 2.44 (2 s, 3H); 2.71 (s, 3H); 4.57 (m, 1H); 5.15 (m, 1H); 6.48 and 6.63 (2 d, 1H); 7.20 (m, 3H); 8.40 and 8.46 (2 d, 1H); 12.90 (s, broad, 1H)*** |
| 41. | 5-methyl-3-phenyl-1,2,4-oxadiazole | 0.93 (t, 3H); 0.96 (s, 9H); 1.33-1.44 (m, 2H); 1.78 (m, 2H); 3.62 (d, 1H); 4.66 (m, 1H); 5.62 (d, 1H); 7.65 (m, 3H); 7.95 (d, 1H); 8.10 (m, 2H); 8.54 (s, 1H); 13.00 (s, 1H)*** |
| 42. | 5-methyl-3-phenyl-1,2,4-oxadiazole | 0.81 (m, 3H); 0.92 (m, 6H); 1.31-1.40 (m, 2H); 1.75 (m, 2H); 2.00 (m, 1H); 3.77 (m, 1H); 4.63 (m, 1H); 5.50 (d, 1H); 7.61 (m, 2H); 7.97 (d, 1H); 8.07 (m, 2H); 8.51 (s, 1H); 12.99 (s, 1H, broad)*** |
| 43. | 5-methyl-3-phenyl-1,2,4-oxadiazole | 0.90 (t, 3H); 1.25-1.40 (m, 2H); 1.82 (m, 2H); 4.63 (m, 1H); 5.16 (d, 1H); 6.63 (d, 1H); 7.18-7.22 (m, 3H); 7.64-7.70 (m, 3H); 8.12 (m, 2H); 8.44 (m, 1H); 8.56 (s, 1H); 13.05 (s, 1H)*** |
| 44. | 1-methyl-5-methyl-tetrazole | 0.88 (t, 3H); 0.91 (t, 9H); 1.32 (m, 2H); 1.71 (m, 2H); 2.42 (s, 3H); 3.56 (d, 1H); 4.09 (s, 3H); 4.57 (m, 1H); 5.58 (d, 1H); 7.84 (d, 1H); 12.63 (s, broad, 1H)*** |
| 45. | N-(2-phenylethyl)methanesulfonamide | 0.93 (t, 3H); 1.40 (m, 2H); 1.70 (m, 2H); 2.48 (s, 3H); 2.77 (m, 2H); 3.14 (m, 2H); 3.62 (d, 1H); 4.51 (m, 1H); 7.03-7.32 (m, 8H); 7.99 (m, 1H); 8.61 (d, 1H); 12.72 (s, broad, 1H)*** |

TABLE 1-continued

| # | Structure | NMR |
|---|---|---|
| 46. | (benzyl-CH₂CH₂-NH-SO₂-CH₃) | 0.94 (t, 3H); 0.98 (s, 9H); 1.35 (m, 2H); 1.76 (m, 2H); 2.48 (s, 3H); 2.78 (t, 2H); 3.15 (m, 2H); 3.63 (d, 1H); 4.63 (m, 1H); 5.62 (d, 1H); 7.21-7.40 (m, 5H); 7.91 (d, 1H); 8.01 (s, 1H, broad); 12.67 (s, 1H)*** |
| 47. | —CN | 0.95 (t, 3H); 0.98 (t, 9H); 1.39 (m, 2H); 1.79 (m, 2H); 3.64 (d, 1H); 4.64 (m, 1H); 5.65 (d, 1H); 7.96 (m, 1H); 8.47 (s, 1H); 13.15 (s, broad, 1H)*** |
| 48. | (1-phenyl-5-methyl-tetrazole) | 0.92 (t, 3H); 0.96 (t, 9H); 1.33 (m, 2H); 1.74 (m, 2H); 3.61 (d, 1H); 4.61 (m, 1H); 5.64 (d, 1H); 7.64 (s, 1H); 7.74-7.82 (m, 5H); 7.92 (m, 1H); 12.75 (s, broad, 1H)*** |
| 49. | (1-phenyl-5-methyl-tetrazole) | 0.87 (t, 3H); 1.28 (m, 2H); 1.75 (m, 2H); 4.55 (m, 1H); 5.12 (d, 1H); 6.60 (d, 1H); 7.17-7.24 (m, 3H); 7.64 (s, 1H); 7.24-7.82 (m, 5H); 8.35 (d, 1H); 12.79 (s, broad, 1H)*** |
| 50. | (1-phenyl-5-methyl-tetrazole) | 0.91 (t, 3H); 1.32 (m, 2H); 1.78 (m, 2H); 4.58 (t, 1H); 5.17 (m, 1H); 6.50 (d, 1H); 7.23 (m, 3H); 7.68 (s, 1H); 7.77-7.86 (m, 5H); 8.45 (m, 1H); 12.85 (s, broad, 1H)*** |
| 51. | (1-benzyl-5-methyl-tetrazole) | 0.94 (t, 3H); 0.97 (t, 9H); 1.35 (m, 2H); 1.77 (m, 2H); 3.63 (m, 1H); 4.65 (m, 1H); 5.64 (d, 1H); 6.00 (s, 2H); 7.25 (m, 2H); 7.40 (m, 3H); 7.92 (d, 1H); 8.17 (s, 1H); 12.79 s, 1H, broad)*** |
| 52. | (benzyl-CH₂CH₂-N(CH₃)-SO₂-CH₃) | 0.90 (t, 3H); 1.33 (m, 2H); 1.68 (m, 2H); 2.47 (s, 3H); 2.80 (s, 3H); 2.68 (t, 2H); 3.30 (t, 2H); 3.59 (m, 2H); 4.46 (m, 1H); 7.01-7.34 (m, 8H); 8.55 (m, broad, 1H); 12.84 (s, broad, 1H)*** |
| 53. | (2-methyl-benzoxazole) | 1.01 (t, 3H); 1.42-1.60 (m, 2H); 1.70-1.90 (m, 2H); 3.71 (s, 2H); 4.67 (m, 1H); 7.12-7.30 (m, 3H); 7.53 (m, 2H); 7.88 (m, 2H); 8.47 (s, 1H); 8.75 (d, 1H); 12.98 (s, 1H, broad)*** |
| 54. | (1-benzyl-5-methyl-tetrazole) | 0.84 (t, 3H); 1.22 (m, 2H); 1.72 (m, 2H); 4.51 (m, 1H); 5.08 (m, 1H); 5.94 (s, 2H); 6.48 (m, 1H); 7.12-7.19 (m, 5H); 7.32-7.39 (m, 3H); 8.1 (s, 1H); 8.35 (m, 1H); 12.77 (s, broad, 1H)*** |

TABLE 1-continued
| | | |
|---|---|---|
| 55. | 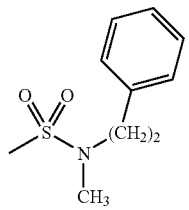 | 0.93 (t, 3H); 0.98 (s, 9H); 1.37 (m, 2H); 1.76 (m, 2H); 2.53 (s, 3H); 2.84 (s, 3H); 2.90 (t, 2H); 3.33 (m, 2H); 3.62 (d, 1H); 4.59 (m, 1H); 5.64 (d, 1H); 7.26-7.45 (m, 5H); 7.91 (m, 1H); 12.60 (s, broad, 1H)*** |
| 56. | 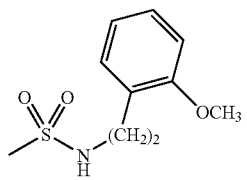 | 0.87 (t, 3H); 0.90 (s, 9H); 1.20 (m, 2H); 1.69 (m, 2H); 2.40 (s, 3H); 2.66 (t, 2H); 3.04 (m, 2H); 3.56 (d, 1H); 3.70 (s, 3H); 4.54 (m, 1H); 5.54 (d, 1H); 6.80-7.20 (m, 4H); 7.84 (d, 1H); 7.92 (s, broad, 1H); 12.60 (s, broad, 1H)*** |
| 57. | 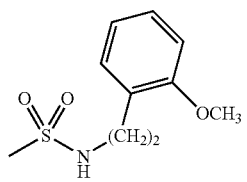 | 0.93 (t, 3H); 1.30-1.50 (m, 2H); 1.73 (m, 2H); 2.45 (s, 3H); 2.72 (t, 2H); 3.11 (m, 2H); 3.63 (s, 2H); 3.74 (s, 3H); 4.51 (m, 1H); 6.80-7.40 (m, 7H); 7.97 (m, 1H); 8.62 (d, 1H); 12.72 (s, 1H)*** |
| 58. | 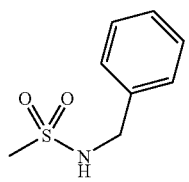 | 0.94 (t, 3H); 1.32-1.44 (m, 2H); 1.71 (m, 2H); 2.46 (s, 3H); 3.63 (m, 2H); 4.51 (m, 1H); 7.05-7.33 (m, 8H); 8.48 (t, 1H); 8.63 (d, 1H); 12.70 (s, 1H, broad)*** |
| 59. | 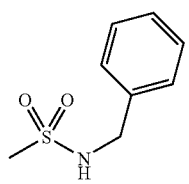 | 0.96 (t, 3H); 1.00 (s, 9H); 1.33-1.47 (m, 2H); 1.78 (m, 2H); 2.48 (s, 3H); 3.65 (d, 1H); 4.17 (d, 2H); 4.63 (q, 1H); 5.64 (d, 1H); 7.30 (m, 5H); 7.93 (m, 1H); 8.51 (s, 1H, broad); 12.50 (s, 1H, broad)*** |
| 60. | 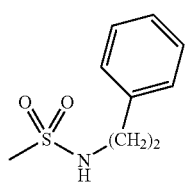 | 0.85 (t, 3H); 1.34 (m, 2H); 1.63 (m, 2H); 2.70 (t, 2H); 3.04 (m, 2H); 3.65 (s, 2H); 4.46 (m, 1H);<br>6.96-7.30 (m, 6H); 7.85 (s, 1H); 7.92 (t, 1H); 8.57 (d, 1H); 12.80 (s, 1H)*** |
| 61. | 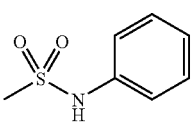 | 0.84 (t, 3H); 0.88 (s, 9H); 1.23 (m, 2H); 1.65 (m, 2H); 2.27 (s, 3H); 3.53 (d, 1H); 4.49 (m, 1H); 5.53 (d, 1H); 7.00-7.30 (m, 5H); 7.81 (d, 1H); 10.40 (s, 1H); 12.59 (s, 1H)*** |
| 62. | 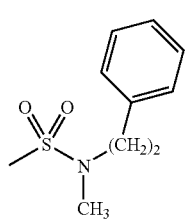 | 0.82 (t, 3H); 1.18-1.28 (m, 2H); 1.71 (m, 2H); 2.46 (s, 3H); 2.77 (s, 3H); 2.83 (m, 2H); 2.72 (m, 2H); 4.48 (m, 1H); 5.07 (d, 1H); 6.54 (d, 1H); 7.10-7.70 (m, 8H); 8.31 (m, 1H); 12.75 (s, 1H)*** |

TABLE 1-continued

| # | Structure | NMR |
|---|---|---|
| 63. | (methanesulfonamide-indane structure) | 0.87 (t, 3H); 1.15-1.30 (m, 2H); 1.66 (m, 2H); 2.48 (s, 3H); 2.79 (m, 2H); 3.03 (m, 2H); 3.56 (m, 2H); 3.97 (m, 1H); 4.46 (m, 1H); 6.97-7.17 (m, 7H); 8.29 (d, 1H); 8.57 (d, 1H); 12.72 (s, 1H)*** |
| 64. | (2,3-dichlorobenzyl methanesulfonamide) | 0.87 (t, 3H); 1.25-1.35 (m, 2H); 1.62-1.68 (m, 2H); 2.41 (s, 3H); 3.56 (m, 2H); 4.22 (m, 2H); 4.43 (m, 1H); 6.99 (m, 2H); 7.08 (m, 1H); 7.28 (m, 1H); 7.39 (m, 1H); 7.50 (m, 1H); 8.56 (m, 2H); 12.68 (s, 1H)*** |
| 65. | (phenethyl methanesulfonamide with tBu) | 0.87 (t, 3H); 0.90 (s, 9H); 1.25-1.28 (m, 2H); 1.70 (m, 2H); 2.72 (t, 2H); 3.06 (m, 2H); 3.57 (d, 1H); 4.57 (m, 1H); 5.54 (d, 1H); 7.18 (m, 3H); 7.25 (m, 2H); 7.86 (m, 1H); 7.89 (s, 1H); 7.94 (m, 1H); 12.74 (s, 1H)*** |
| 66. | (indane methanesulfonamide with tBu) | 0.87 (t, 3H); 0.91 (s, 9H); 1.20-1.35 (m, 2H); 1.69 (m, 2H); 2.48 (s, 3H); 2.79 (m, 2H); 3.03 (m, 2H); 3.56 (d, 1H); 3.98 (m, 1H); 4.56 (m, 1H); 5.57 (d, 1H); 7.10-7.17 (m, 4H); 7.86 (m, 1H); 8.31 (m, 1H); 12.63 (s, 1H)*** |
| 67. | (phenethyl methanesulfonamide) | 0.81 (t, 3H); 1.17-1.30 (m, 2H); 1.70 (m, 2H); 2.70 (m, 2H); 3.04 (s, 3H); 4.50 (m, 1H); 5.06 (m, 1H); 6.52 (d, 1H); 7.11-7.24 (m, 8H); 7.87 (s, 1H); 7.95 (m, 1H); 8.33 (d, 1H); 12.76 (s, 1H)*** |
| 68. | (phenethyl methanesulfonamide) | 0.84 (t, 3H); 1.22-1.34 (m, 2H); 1.72 (m, 2H); 2.71 (m, 2H); 3.05 (m, 2H); 4.49 (m, 1H); 5.10 (d, 1H); 6.43 (d, 1H); 7.12-7.25 (m, 8H); 7.87 (s, 1H); 7.94 (m, 1H); 8.39 (d, 1H); 12.80 (s, 1H, broad)*** |
| 69. | (2,3-dichlorobenzyl methanesulfonamide) | 0.83 (t, 3H); 1.18-1.29 (m, 2H); 1.71 (m, 2H); 2.41 (s, 3H); 4.23 (m, 2H); 4.49 (m, 1H); 5.08 (d, 1H); 6.55 (d, 1H); 7.15 (m, 3H); 7.29 (t, 1H); 7.39 (d, 1H); 7.51 (d, 1H); 8.33 (d, 1H); 8.61 (t, 1H); 12.64 (s, 1H)*** |
| 70. | (2,3-dichlorobenzyl methanesulfonamide) | 0.82 (t, 3H); 1.20-1.30 (m, 2H); 1.69 (m, 2H); 2.39 (s, 3H); 4.20 (m, 2H); 4.44 (m, 1H); 5.08 (d, 1H); 6.41 (d, 1H); 7.12 (m, 3H); 7.2 (t, 1H); 7.36 (d, 1H); 7.47 (d, 1H); 8.36 (d, 1H); 8.58 (m, 1H); 12.66 (s, 1H)*** |
| 71. | (benzyl methanesulfonamide) | 0.94 (t, 3H); 1.30-1.44 (m, 2H); 1.69-1.76 (m, 2H); 2.46 (s, 3H); 3.63 (m, 2H); 4.14 (m, 2H); 4.51 (m, 1H); 7.06 (m, 2H); 7.15 (m, 1H); 7.25-7.33 (m, 5H); 8.48 (t, 1H); 8.63 (d, 1H); 12.70 (s, 1H, broad)*** |

TABLE 1-continued
| 72. | 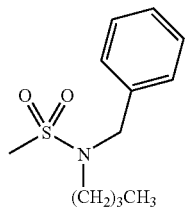 | 0.69 (t, 3H); 0.87 (t, 3H); 1.09 (m, 2H); 1.27 (m, 2H); 1.35 (m, 2H); 1.66 (m, 2H); 3.10 (m, 2H); 3.56 (m, 2H); 4.34 (s, 2H); 4.44 (m, 1H); 6.98 (m, 2H); 7.08 (m, 1H); 7.25-7.36 (m, 5H); 8.59 (d, 1H); 12.82 (s, 1H)*** |
| --- | --- | --- |
| 73. | 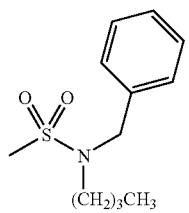 | 0.69 (t, 3H); 0.87 (t, 3H); 0.91 (s, 9H); 1.09 (m, 2H); 1.26 (m, 2H); 1.70 (m, 2H); 3.11 (m, 2H); 3.56 (d, 1H); 4.35 (s, 2H); 4.55 (m, 1H); 5.57 (d, 1H); 7.27-7.36 (m, 5H); 7.86 (s, 1H); 12.73 (s, 1H)**** |
| 74. | 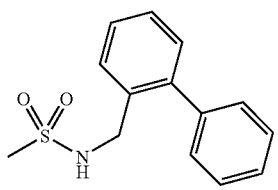 | 0.88 (t, 3H); 1.25-1.35 (m, 2H); 1.68 (m, 2H); 2.28 (s, 3H); 3.57 (m, 2H); 3.99 (d, 2H); 4.45 (m, 1H); 6.99-7.45 (m, 12H); 8.32 (t, 1H); 8.58 (d, 1H); 12.64 (s, 1H)**** |
| 75. | 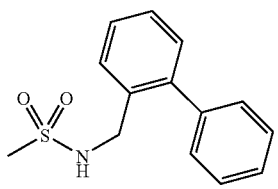 | 0.88 (t, 3H); 0.91 (s, 9H); 1.25-1.35 (m, 2H); 1.70 (m, 2H); 2.29 (s, 3H); 3.57 (d, 1H); 4.00 (d, 2H); 5.55 (d, 1H); 7.15-7.45 (m, 9H); 7.86 (d, 1H); 8.33 (t, 1H); 12.56 (s, 1H)**** |
| 76. | 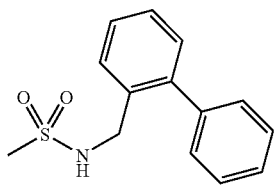 | 0.79 (d, 3H); 0.89 (d, 3H); 0.90 (t, 3H); 1.20-1.40 (m, 2H); 1.71 (m, 2H); 1.98 (m, 1H); 2.29 (s, 3H); 3.75 (m, 1H); 4.00 (d, 2H); 4.56 (m, 1H); 5.47 (d, 1H); 7.15-7.50 (m, 9H); 7.91 (d, 1H); 8.33 (t, 1H); 12.59 (s, 1H)**** |
| 77. | 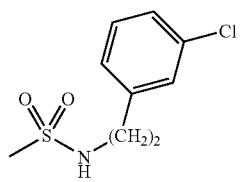 | 0.87 (t, 3H); 0.90 (s, 9H); 1.20-1.35 (m, 2H); 1.68 (m, 2H); 2.59 (s, 3H); 2.72 (m, 2H); 3.11 (m, 2H); 3.56 (d, 1H); 4.55 (m, 1H); 5.55 (d, 1H); 7.11-7.27 (m, 4H); 7.84 (d, 1H); 7.94 (m, 1H); 12.60 (s, 1H)**** |
| 78. | 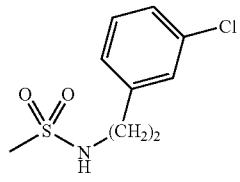 | 0.86 (t, 3H); 1.25-1.35 (m, 2H); 1.65 (m, 2H); 2.38 (s, 3H); 2.71 (m, 2H); 3.11 (m, 2H); 3.56 (m, 2H); 4.45 (m, 1H); 6.90-7.30 (m, 7H); 7.93 (m, 1H); 8.57 (d, 1H); 12.68 (s, 1H)**** |
| 79. | 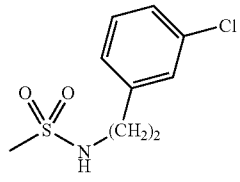 | 0.77 (d, 3H); 0.86 (t, 3H); 0.91 (d, 3H); 1.24-1.35 (m, 2H); 1.70 (m, 2H); 1.95 (m, 1H); 2.38 (s, 3H); 2.72 (m, 2H); 3.11 (m, 2H); 3.73 (m, 1H); 4.55 (m, 1H); 5.47 (d, 1H); 7.11-7.27 (m, 4H); 7.89 (d, 1H); 7.94 (q, 1H); 12.63 (s, 1H)**** |

TABLE 1-continued

| | | |
|---|---|---|
| 80. | 5-methyl-3-benzyl-1,2,4-oxadiazole | 0.87 (t, 3H); 0.90 (s, 9H); 1.27-1.37 (m, 2H); 1.73 (m, 2H); 3.57 (d, 2H); 4.18 (s, 2H); 4.58 (m, 1H); 5.52 (d, 1H); 7.26-7.34 (m, 5H); 7.90 (d, 1H); 13.29 (s, 1H)\*\*\*\* |

| Cpd | R₅ | MH⁺ |
|---|---|---|
| 81. | 2-methylphenyl phenyl ether | 549 |
| 82. | 2-methylphenyl phenyl ether | 589 |
| 83. | —CH(CH₃)₂ | 423 |
| 84. | —CH(CH₃)₂ | 463 |
| 85. | methanesulfonamido-(2,3-dichlorobenzyl) | 591 |
| 86. | methanesulfonamido-(2,3-dichlorobenzyl) | 551 |
| 87. | methanesulfonamido-(2,3-dichlorobenzyl) | 537 |
| 88. | methanesulfonamido-(2,3-dichlorobenzyl) | 577 |
| 89. | methanesulfonamido-(2,3-dichlorobenzyl) | 537 |
| 90. | methanesulfonamido-(2,3-dichlorobenzyl) | 523 |
| 91. | methanesulfonamido-methyl | 421 |

TABLE 1-continued

| | | |
|---|---|---|
| 92. | methanesulfonamide, N-methyl | 461 |
| 93. | methanesulfonamide, N-methyl | 477 |
| 94. | N-(1-phenylethyl)methanesulfonamide | 551 |
| 95. | N-(1-phenylethyl)methanesulfonamide | 551 |
| 96. | N-(1-phenylethyl)methanesulfonamide | 511 |
| 97. | N-(1-phenylethyl)methanesulfonamide | 511 |
| 98. | N-(2,3-dihydro-1H-inden-2-yl)methanesulfonamide | 579 |
| 99. | N-(2,3-dihydro-1H-inden-2-yl)methanesulfonamide | 579 |
| 100. | N-(1-phenylethyl)methanesulfonamide | 497 |
| 101. | N-(1-(naphthalen-1-yl)ethyl)methanesulfonamide | 561 |

TABLE 1-continued
| | | |
|---|---|---|
| 102. | 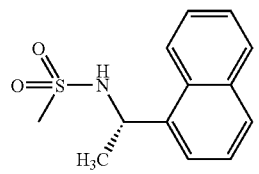 | 601 |
| 103. | 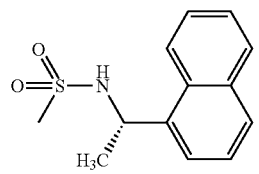 | 617 |
| 104. | 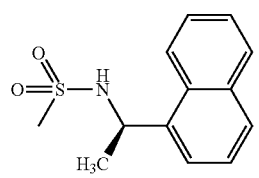 | 561 |
| 105. | 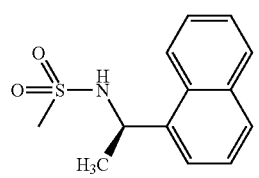 | 601 |
| 106. | 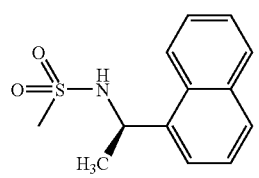 | 617 |
| 107. | 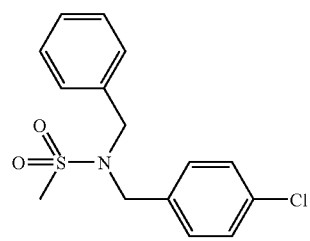 | 621 |
| 108. | 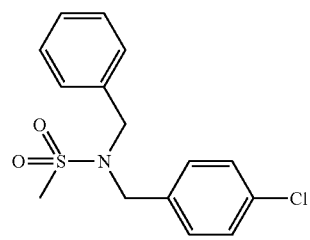 | 661 |
| 109. | 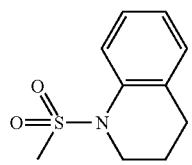 | 637 |

TABLE 1-continued
| | | |
|---|---|---|
| 110. | 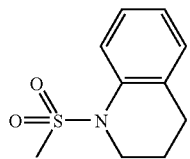 | 563 |
| 111. | 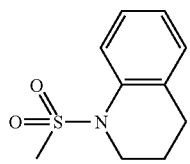 | 579 |
| 112. | 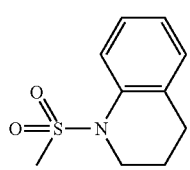 | 579 |
| 113. | 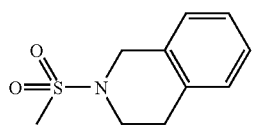 | 523 |
| 114. | 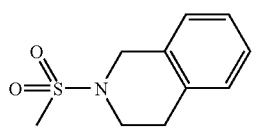 | 563 |
| 115. | 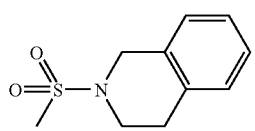 | 579 |
| 116. | 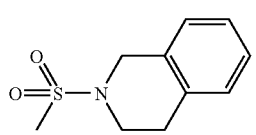 | 579 |
| 117. | 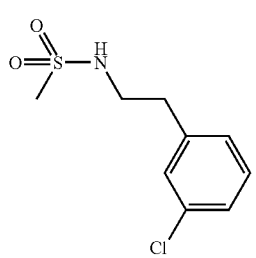 | 601 |
| 118. | 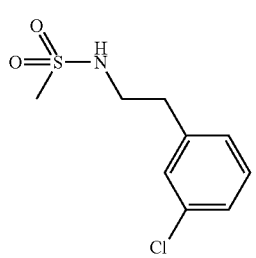 | 601 |

TABLE 1-continued
| | | |
|---|---|---|
| 119. | 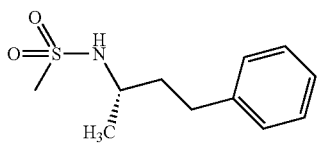 | 539 |
| 120. | 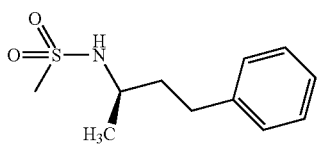 | 539 |
| 121. | 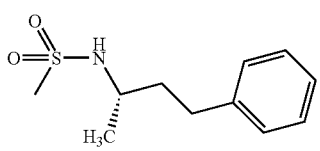 | 579 |
| 122. | 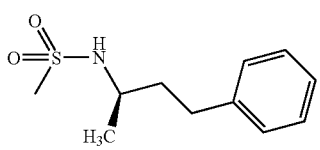 | 579 |
| 123. | 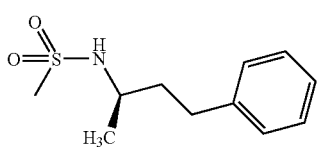 | 595 |
| 124. | 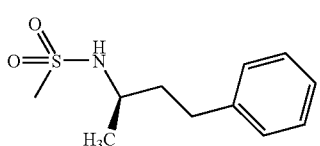 | 595 |
| Cpd | $R_5$ | NMR (DMSO d6 unless specified) |
|---|---|---|
| 125. | 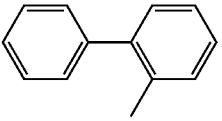 | 0.86 (t, 3H); 0.90 (s, 9H); 1.30 (m, 2H); 1.68 (m, 2H); 3.55 (d, 1H); 4.54 (m, 1H); 5.59 (d, 1H); 6.80 (s, 1H); 7.04-7.57 (m, 9H); 7.77 (d, 1H); 8.19 (s, 1H); 12.41 (s, broad, 1H)**** |
| 126. | 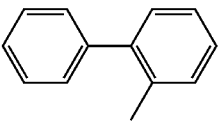 | 0.77 and 0.90 (2 d, 6H); 0.87 (t, 9H); 1.24 (m, 2H); 1.69 (m, 2H); 1.97 (m, 2H); 3.78 (m, 1H); 4.54 (m, 1H); 5.48 (d, 1H); 6.80 (s, 1H); 7.04-7.56 (m, 9H); 7.82 (d, 1H); 8.18 (s, 1H); 12.44 (s, broad, 1H)**** |
| 127. | 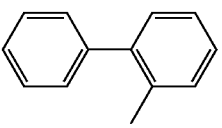 | 0.87 (t, 3H); 1.30 (m, 2H); 1.65 (m, 2H); 3.56 (m, 2H); 4.44 (m, 1H); 6.79 (s, 1H); 6.97-7.56 (m, 12H); 8.18 (s, 1H); 8.48 (d, 1H); 12.51 (s, 1H)**** |
| 128. | 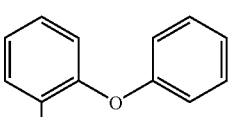 | 0.87 (t, 3H); 0.91 (s, 9H); 1.28 (m, 2H); 1.70 (m, 2H); 3.55 (d, 1H); 4.56 (m, 1H); 5.58 (d, 1H); 6.79-7.50 (m, 10H); 7.78 (d, 1H); 8.32 (s, 1H); 12.52 (s, 1H)**** |

TABLE 1-continued
| | | |
|---|---|---|
| 129. | 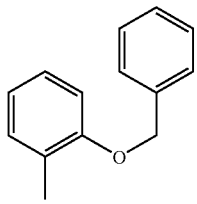 | 0.88 (t, 3H); 0.92 (s, 9H); 1.30 (m, 2H); 1.72 (m, 2H); 3.57 (d, 1H); 4.58 (m, 1H); 5.08 (s, 2H); 5.59 (d, 1H); 7.02-7.43 (m, 10H); 7.81 (d, 1H); 8.25 (s, 1H); 12.50 (s, 1H)**** |
| 130. | 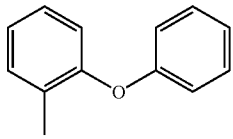 | 0.87 (t, 3H); 1.32 (m, 2H); 1.65 (m, 2H); 3.56 (m, 2H); 4.46 (m, 1H); 6.79-7.50 (m, 13H); 8.32 (s, 1H); 8.49 (d, 1H); 12.58 (s, 1H)**** |
| 131. | 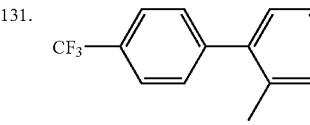 | 0.88 (t, 3H); 0.91 (s, 9H); 1.30 (m, 2H); 1.70 (m, 2H); 2.24 (s, 3H); 3.57 (d, 1H); 4.56 (m, 1H); 5.58 (d, 1H); 7.23-7.63 (m, 8H); 7.83 (d, 1H); 8.25 (s, 1H); 12.65 (s, 1H)**** |
| 132. | 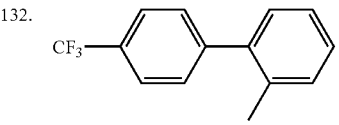 | 0.78 and 0.91 (2 d, 6H); 0.88 (t, 3H); 1.28 (m, 2H); 1.72 (m, 2H); 1.98 (m, 1H); 2.23 (s, 3H); 3.75 (m, 1H); 4.56 (m, 1H); 5.47 (d, 1H); 7.23-7.63 (m, 8H); 7.88 (d, 1H); 12.69 (s, 1H)**** |
| 133. | 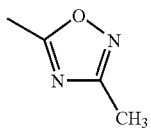 | 0.87 (t, 3H); 0.90 (s, 9H); 1.31 (m, 2H); 1.70 (m, 2H); 2.20 (s, 3H); 3.56 (d, 1H); 4.57 (m, 1H); 5.55 (d, 1H); 7.17 (d, 2H); 7.50-7.65 (m, 6H); 7.86 (d, 1H); 12.87 (s, 1H, broad)**** |
| 134. | 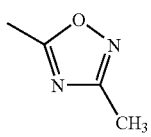 | 0.78 and 0.91 (2 d, 6H); 0.87 (t, 3H); 1.30 (m, 2H); 1.71 (m, 2H); 1.98 (m, 1H); 2.20 (s, 3H); 3.74 (m, 1H); 4.57 (m, 1H); 5.45 (d, 1H); 7.18 (d, 2H); 7.50-7.65 (m, 6H); 7.90 (d, 1H); 12.90 (s, 1H, broad)**** |
| 135. | 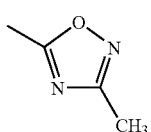 | 0.86 (t, 3H); 1.34 (m, 2H); 1.66 (m, 2H); 2.20 (s, 3H); 3.55 (m, 2H); 4.48 (m, 1H); 6.98 (d, 2H); 7.07 (t, 1H); 7.17 (d, 2H); 7.47-7.65 (m, 6H); 8.59 (d, 1H); 12.96 (s, 1H)**** |
| 136. | 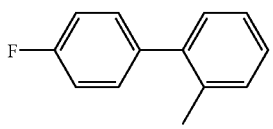 | 0.83-0.99 (m, 9H); 1.23-1.43 (m, 2H); 1.78 (m, 2H); 2.05 (m, 1H); 2.31 (s, 3H); 3.81 (m, 1H); 4.61 (m, 1H); 5.57 (d, 1H); 7.11 (m, 4H); 7.48-7.6 (m, 4H); 7.96 (d, 1H); 12.80 (s, 1H)**** |
| 137. | 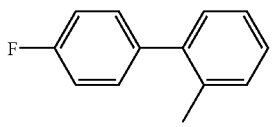 | 0.88 (t, 3H); 0.92 (s, 9H); 1.24-1.41 (m, 2H); 1.72 (m, 2H); 1.99 (s, 3H); 3.57 (d, 1H); 4.55 (m, 1H); 5.63 (d, 1H); 7.10-7.20 (m, 4H); 7.40-7.60 (m, 4H); 7.86 (d, 1H); 12.67 (s, 1H)**** |
*signifies 300 MHz -
**signifies 360 MHz -
***signifies 500 MHz -
****signifies 600 MHz In the table:

(S) or (R) in the columns "$R_3$" and "$R_2$, $R'_2$" indicates the stereochemistry of the asymmetric carbon carrying $R_3$ or $R_2$ in the formula (I). For the carbon carrying $R_2$ the indication (S) or (R) does not relate to the case where $R_2$ and $R'_2$ together form an oxo group;

MH$^+$ is the value of the mass of the compound protonated by a hydrogen atom (mass of the compound+1), as determined by LC-MS.

The compounds of the invention were subjected to pharmacological tests, which showed their advantage as active substances in therapy.

They were tested in particular for their inhibitory effects on the production of the β-amyloid peptide (β-A4).

β-Amyloid peptide (β-A4) is a fragment of a larger precursor protein called APP (amyloid precursor protein). The latter is produced and is present in various cells of human or animal tissue. However its cleavage in cerebral tissue by protease-type enzymes leads to the formation of the β-A4 peptide, which accumulates in the form of an amyloid plaque. The two proteases responsible for producing the amyloid peptide are known by the name of beta- and gamma-secretases (Wolfe M S, Secretase targets for Alzheimer's disease: identification and therapeutic potential, J. Med. Chem. 2001, 44 (13): 2039-60).

It has been demonstrated that this gradual deposition of the β-A4 peptide is neurotoxic and might play an important role in Alzheimer's disease.

Accordingly the compounds of the present invention, as an inhibitor of the production of the β-amyloid peptide (β-A4) by inhibition of gamma-secretase, can be used in the treatment of pathologies such as senile dementia, Alzheimer's disease, Down's syndrome, Parkinson's disease, amyloid angiopathy and/or cerebrovascular disorders, frontotemporal dementias and Pick's disease, post-traumatic dementias, pathologies linked to neuroinflammatory processes, Huntington's disease and Korsakov's syndrome.

The tests were conducted in accordance with the protocol described below.

For the β-amyloid cellular test, the CHO—K1 line coexpressing the CT100 of APP and PS1 M146L clone 30-12 is used. The line targets the inhibition of gamma-secretase. Presenilin is linked to gamma-secretase activity (Wolfe M S, Haass C., The Role of presenilins in gamma-secretase activity, J. Biol. Chem. 2001, 276(8): 5413-6) and its coexpression with the amyloid protein or its N-terminal fragment causes an increase in secretion of the peptide A1-42 (β-A4), thereby generating a pharmacological tool which allows inhibition by the compounds of formula (I) of the production of the β-A4 peptide to be evaluated. 96-well culture plates are inoculated with 1×10$^5$ cells per well in 150 µl of incubation medium. The presence of a minimum percentage (1.3% final) of serum allows cellular adhesion to the plastic after 2-3 hours of incubation at 37° C., in the presence of 5% $CO_2$. The products (15 µl) are tested at 10 µM DMSO 1% final and are incubated for 24-25 h at 37° C. in the presence of 5% $CO_2$ and 100% humidity. After this 24-25 h incubation, the cellular supernatants (100 µl) are transferred to ELISA plates, treated with the capture antibody 6E10 (6E10, epitope: aa1-17, INTERCHIM/SENETEK 320/10), to determine the amount of amyloid peptides secreted by the cells in the presence of compounds according to the invention. A series of synthetic control peptide, "peptide 1-40", at 5 and 10 ng/ml is treated in parallel. The ELISA plates are incubated overnight at 4° C.

The quantity of bound peptide is detected indirectly in the presence of a competitor which corresponds to the truncated peptide, peptide 1-28 coupled to biotin, which is then detected with streptavidin coupled to alkaline phosphatase. The substrate, p-nitrophenyl phosphate (pNPP FAST p-Nitrophenyl Phosphate, Sigma N2770), gives a yellow, soluble reaction product which can be read at 405 nm. The reaction is stopped with 0.1 M EDTA solution. For this purpose, following binding of the amyloid peptide in the ELISA plate, 50 µl of biotinylated peptide 1-28 are added to 100 µl of cellular supernatant and incubated for 30 minutes at ambient temperature. The ELISA plates are then washed 3 times. After drying by inversion on absorbent paper, 100 µl of streptavidin-alkaline phosphatase (Interchim/Jackson ImmunoResearch Laboratories 016-050-084) are added per well and incubated for 1 hour at ambient temperature. The plates are washed again and then the alkaline phosphatase substrate (pNPP 1 mg/ml) is added in an amount of 100 µl per well. After 30 minutes of incubation at ambient temperature the reaction is stopped by adding 100 µl per well of 0.1 M EDTA and reading is carried out at 405 nm.

The most active compounds of formula (I) according to the present invention showed an $EC_{50}$ (50% effective concentration) of less than 500 nM, more particularly less than 100 nM.

Table 2 below gives the $EC_{50}$ values of several compounds according to the invention.

TABLE 2

| Compound | $EC_{50}$ (nM) |
| --- | --- |
| 7 | 52 |
| 34 | 42 |
| 40 | 85 |
| 51 | 94 |

The results of biological tests show that the compounds are inhibitors of the formation of the β-amyloid peptide (β-A4).

Accordingly these compounds can be employed in the treatment of pathologies in which a β-amyloid peptide (β-A4) formation inhibitor provides a therapeutic benefit. Particular such pathologies are senile dementia, Alzheimer's disease, Down's syndrome, Parkinson's disease, amyloid angiopathy, cerebrovascular disorders, frontotemporal dementias and Pick's disease, post-traumatic dementias, pathologies linked to neuroinflammatory processes, Huntington's disease and Korsakov's syndrome.

The use of the compounds according to the invention for preparing a medicinal product intended for treating the abovementioned pathologies forms an integral part of the invention.

The invention further provides medicinal products which comprise a compound of formula (I), or an addition salt thereof with a pharmaceutically acceptable acid or else a hydrate or a solvate of the compound of formula (I). These medicinal products find their use in therapy, in particular in the treatment of the abovementioned pathologies.

In another of its aspects the present invention relates to pharmaceutical compositions comprising as active principle at least one compound according to the invention. These pharmaceutical compositions comprise an effective dose of a compound according to the invention, or of a pharmaceutically acceptable salt, hydrate or solvate of the said compound, and, optionally, one or more pharmaceutically acceptable excipients.

The said excipients are selected, according to the pharmaceutical form and the desired mode of administration, from the customary excipients which are known to the person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its salt, its solvate or its hydrate where appropriate, can be administered in unit form for administration, as a mixture with conventional pharmaceutical excipients, to animals and to humans for the prophylaxis or treatment of the above diseases or disorders.

The appropriate unit forms for administration embrace the forms for oral administration such as tablets, soft or hard gelatin capsules, powders, granules, chewing gums and oral solutions or suspensions, the forms for sublingual, buccal, intratracheal, intraocular or intranasal administration or for administration by inhalation, the forms for subcutaneous, intramuscular or intravenous administration and the forms for rectal or vaginal administration. For topical application the compounds according to the invention can be used in creams, ointments or lotions.

By way of example, a unit form for administration of a compound according to the invention in tablet form may comprise the following components:

| Compound according to the invention | 50.0 mg |
|---|---|
| Mannitol | 223.75 mg |
| Croscaramellose sodium | 6.0 mg |
| Maize starch | 15.0 mg |
| Hydroxypropylmethylcellulose | 2.25 mg |
| Magnesium stearate | 3.0 mg |

In order to obtain the desired therapeutic or prophylactic effect, the dose of active principle may vary between 0.1 mg and 200 mg per kg of body weight per day. Although these dosages are average-situation examples, there may be particular cases in which higher or lower dosages are appropriate: such dosages are likewise part of the invention. In accordance with customary practice, the dosage appropriate to each patient is determined by the doctor in accordance with the mode of administration, the weight and the response of the said patient.

Each unit dose can contain from 0.1 to 1000 mg, preferably from 0.1 to 500 mg, of active principle in combination with one or more pharmaceutical excipients. This unit dose can be administered from 1 to 5 times per day, in order to administer a daily dosage of from 0.5 to 5000 mg, preferably from 0.5 to 2500 mg.

In another of its aspects the present invention likewise relates to a method of treating the pathologies indicated above which comprises administering a compound according to the invention, a pharmaceutically acceptable salt or a hydrate of the said compound.

The invention claimed is:

1. A compound having the general formula (I):

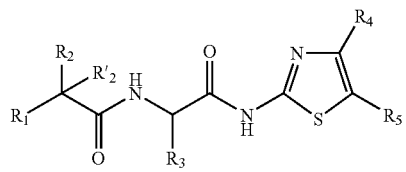

in which $R_1$ represents either a $C_{1-6}$ alkyl optionally substituted by one to three substituents selected from halogen, trifluoromethyl, hydroxyl, $C_{1-6}$ alkoxy, $C_{1-6}$ thioalkyl, thiophene and phenyl; or a $C_{3-7}$ cycloalkyl, or a thiophene, or a benzothiophene, or a pyridinyl, or a furanyl or a phenyl; the said phenyl groups being optionally substituted by one to three substituents selected from halogen, $C_{1-6}$ alkyl, $C_{1-6}$ alkoxy, hydroxyl, methylenedioxy, phenoxy, benzyloxy and trifluoromethyl;

$R_2$ and $R'_2$ represent, independently of one another, a substituent selected from hydrogen, halogen, hydroxyl, $C_{1-3}$ alkoxy, $C_{1-3}$ alkyl, $C_{3-7}$ cycloalkyl and O—C(O)—$C_{1-6}$ alkyl group, or $R_2$ and $R'_2$ together form an oxo group;

$R_3$ represents either hydrogen or $C_{1-6}$ alkyl optionally substituted by hydroxyl, $C_{1-6}$ cycloalkyl or $C_{1-3}$ alkoxy;

$R_4$ is Z and $R_5$ is L or $R_4$ is L and $R_5$ is Z; wherein the group L is:

in which G represents a $C_{1-7}$ alkyl or a single bond;

M represents a $C_{3-7}$ cycloalkyl, a phenyl, a naphthyl or a pyridinyl, the group M being optionally substituted by one or more groups selected from halogen, hydroxyl, $C_{1-3}$ alkyl, $C_{1-3}$ alkoxy, trifluoromethyl, trifluoromethoxy and —O—CHF$_2$; and J represents hydrogen or a group —Y—K; wherein Y represents a single bond, oxygen, sulphur, —$C_{1-4}$ alkylene-, —O—$C_{1-4}$ alkylene- or —$C_{1-4}$ alkylene-O— or a group —N(W)—, the —$C_{1-4}$ alkylene-being optionally substituted by a hydroxyl or $C_{1-3}$ alkoxy;

W represents either hydrogen, $C_{1-3}$ alkyl optionally substituted by phenyl, or phenyl; and K represents a phenyl or pyridinyl group, the group K being optionally substituted by one or more groups selected from halogen, hydroxyl, $C_{1-3}$ alkyl, $C_{1-3}$ alkoxy, trifluoromethyl, trifluoromethoxy and —O—CHF$_2$;

Z represents CN, SO$_2$NR$_6$R$_7$ or a heteroaromatic group, the said heteroaromatic group being optionally substituted by a group $R_8$; $R_8$ representing either a $C_{1-4}$ alkyl which is itself optionally substituted by a CN, a phenyl or a phenoxy; or a phenyl; the said phenyl and phenoxy groups being optionally substituted by 1 to 3 groups selected from halogen, $C_{1-3}$ alkyl, $C_{1-3}$ alkoxy and trifluoromethyl; and $R_6$ and $R_7$ represent, independently of one another, either hydrogen, or $C_{1-6}$ alkyl optionally substituted by $C_{3-7}$ cycloalkyl, $C_{3-7}$ cycloalkenyl, $C_{1-3}$ alkoxy, phenyl, naphthalenyl, morpholinyl or pyridinyl; or $C_{3-7}$ cycloalkyl, $C_{1-6}$ alkoxy, phenyl or indanyl; the said $C_{3-7}$ cycloalkyl, $C_{3-7}$ cycloalkenyl, phenyl, naphthalenyl, morpholinyl, pyridinyl and indanyl groups being optionally substituted by one or two groups selected from $C_{1-3}$ alkyl, hydroxyl, $C_{1-3}$ alkoxy, phenyl or halogen; or $R_6$ and $R_7$, together with the nitrogen atom to which they are attached, form an aziridine, azetidine, pyrrolidine, piperidine, morpholine or benzopiperidine ring; or a pharmaceutically acceptable salt thereof.

2. The compound according to claim 1, wherein:

$R_1$ represents a $C_{1-6}$ alkyl or a phenyl which is optionally substituted by 1 to 3 halogen atoms;

$R_2$ and $R'_2$ represent, independently of one another, hydrogen or hydroxyl;

$R_3$ represents $C_{1-6}$ alkyl;

G represents a $C_{1-7}$ alkyl or a single bond;

M represents a phenyl which is optionally substituted by one or more halogens;

J represents hydrogen or a group —Y—K;

Y represents a single bond, oxygen or —O—$C_{1-4}$ alkylene-;

K represents a phenyl group which is optionally substituted by one or more groups selected from halogen, $C_{1-3}$ alkyl and trifluoromethyl;

Z represents CN, $SO_2NR_6R_7$ or a heteroaromatic group, said heteroaromatic group being optionally substituted by a group $R_8$; $R_8$ representing either $C_{1-4}$ alkyl which is itself optionally substituted by phenyl; or phenyl; and $R_6$ and $R_7$ represent, independently of one another, either hydrogen, or $C_{1-6}$ alkyl optionally substituted by phenyl or by naphthalenyl; or a phenyl or an indanyl; said phenyl groups being optionally substituted by one or two groups selected from $C_{1-3}$ alkoxy, phenyl or halogen; or $R_6$ and $R_7$, together with the nitrogen atom to which they are attached, form a benzopiperidine ring; or a pharmaceutically acceptable salt thereof.

3. The compound of formula (I) according to claim 1, wherein:

$R_1$ represents $C_{1-4}$ alkyl, or a phenyl substituted by two fluorine atoms;

$R_2$ and $R'_2$ represent, independently of one another, hydrogen or hydroxyl; and $R_3$ represents $C_{1-4}$ alkyl; or a pharmaceutically acceptable salt thereof.

4. The compound of claim 3 wherein $R_1$ is selected from isopropyl and tert-butyl.

5. The compound of claim 3 wherein $R_3$ is selected from methyl, ethyl and propyl.

6. A pharmaceutical composition comprising at least one compound of formula (I) according to claim 1, in the form of a pharmaceutically acceptable base, or salt, said composition further comprising one or more pharmaceutically acceptable excipients.

\* \* \* \* \*